United States Patent
Kim et al.

(10) Patent No.: US 12,173,325 B2
(45) Date of Patent: Dec. 24, 2024

(54) METHOD FOR FABRICATION OF THREE-DIMENSIONAL LUNG ORGANOID COMPRISING HUMAN STEM CELL-DERIVED ALVEOLAR MACROPHAGE

(71) Applicant: KOREA RESEARCH INSTITUTE OF CHEMICAL TECHNOLOGY, Daejeon (KR)

(72) Inventors: Eun-Mi Kim, Daejeon (KR); Ki-Suk Kim, Daejeon (KR); Hyang-Ae Lee, Daejeon (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 630 days.

(21) Appl. No.: 17/283,942

(22) PCT Filed: Dec. 20, 2019

(86) PCT No.: PCT/KR2019/018219
§ 371 (c)(1),
(2) Date: Apr. 8, 2021

(87) PCT Pub. No.: WO2020/130713
PCT Pub. Date: Jun. 25, 2020

(65) Prior Publication Data
US 2021/0395695 A1   Dec. 23, 2021

(30) Foreign Application Priority Data
Dec. 20, 2018   (KR) .................. 10-2018-0166267

(51) Int. Cl.
C12N 5/071      (2010.01)
C12M 3/00       (2006.01)
C12N 5/0786     (2010.01)

(52) U.S. Cl.
CPC ........... *C12N 5/0688* (2013.01); *C12M 21/08* (2013.01); *C12N 5/0645* (2013.01); *C12N 5/0697* (2013.01); *C12N 2501/117* (2013.01); *C12N 2501/119* (2013.01); *C12N 2501/15* (2013.01); *C12N 2501/155* (2013.01); *C12N 2501/999* (2013.01); *C12N 2513/00* (2013.01)

(58) Field of Classification Search
None
See application file for complete search history.

(56) References Cited

U.S. PATENT DOCUMENTS

2013/0217005 A1   8/2013   Snoeck et al.

FOREIGN PATENT DOCUMENTS

WO   WO 2018/176044 A1   9/2018

OTHER PUBLICATIONS

Ana Ivonne Vazquez Armendariz, Establishment of murine 3D bronchioalveolar lung organoids from adult somatic stem cells for organ development and disease modeling, doctoral defense, Sep. 26, 2018. (Year: 2018).*
Magro-Lopez, Esmeralda, et al. "Effects of lung and airway epithelial maturation cocktail on the structure of lung bud organoids." Stem Cell Research & Therapy 9.1 (2018): 1-6. (Year: 2018).*
Kadzik, Rachel S., and Edward E. Morrisey. "Directing lung endoderm differentiation in pluripotent stem cells." Cell stem cell 10.4 (2012): 355-361. (Year: 2012).*
Evseenko, Denis, et al. "Mapping the first stages of mesoderm commitment during differentiation of human embryonic stem cells." Proceedings of the National Academy of Sciences 107.31 (2010): 13742-13747. (Year: 2010).*
Holtzinger, Audrey, et al. "New markers for tracking endoderm induction and hepatocyte differentiation from human pluripotent stem cells." Development 142.24 (2015): 4253-4265. (Year: 2015).*
Chen et al., "A Three-Dimensional Model of Human Lung Development and Disease from Pluripotent Stem Cells," *Nature Cell Biology 19.5*: 542-557, May 2017.
Dye et al., "In Vitro Generation of Human Pluripotent Stem Cell Derived Lung Organoids," *eLife 4*: e05098, Mar. 2015 (25 pages).
Happle et al., "Induced Pluripotent Stem Cell Derived Macrophages Differentiate into AM Like Cells in the Lungs of Humanized PAP Mice," *European Respiratory Journal 50*: PA4177, 2017 (Abstract).
He et al., "Exposure to Ambient Particulate Matter Induced COPD in a Rat Model and a Description of the Underlying Mechanism," *Scientific Reports 7*: 45666, Mar. 2017 (15 pages).
International Search Report and Written Opinion for PCT/KR2019/018219, mailed Apr. 6, 2020, ISA Korean Intellectual Property Office, 7 pages (w/English translation of International Search Report, 3 pages).
Lam et al., "Rapid and Efficient Differentiation of Human Pluripotent Stem Cells into Intermediate Mesoderm that Forms Tubules Expressing Kidney Proximal Tubular Markers," *J Am Soc Nephrol. 25*: 1211-1225, 2014.
Magro-Lopez et al., "Effects of Lung and Airway Epithelial Maturation Cocktail on the Structure of Lung Bud Organoids," *Stem Cell Research & Therapy 9*: 186, 2018 (6 pages).

(Continued)

Primary Examiner — Emily A Cordas
Assistant Examiner — Constantina E Stavrou
(74) Attorney, Agent, or Firm — Klarquist Sparkman, LLP

(57) ABSTRACT

The present invention relates to a method for fabrication of a three-dimensional lung organoid comprising human stem cell-derived alveolar macrophages. Specifically, a lung organoid is fabricated by co-culturing cells not expressing the definitive endoderm marker CRCX4 according to a fabrication method of the present disclosure. The lung organoid comprises type 1 and type 2 alveolar epithelial cells as well as alveolar macrophages and realizes infectious or inflammatory responses unlike conventional lung organoids that contain no immune cells and as such, can be advantageously used in studying mechanisms of related lung diseases, excavating biomarkers, developing therapeutic agents, and so on.

12 Claims, 27 Drawing Sheets

Specification includes a Sequence Listing.

(56) References Cited

OTHER PUBLICATIONS

Rice et al., "Long-Term Exposure to Traffic Emissions and Fine Particulate Matter and Lung Function Decline in the Framingham Heart Study," *American Journal of Respiratory and Critical Care Medicine 191.6*: 656-664, Mar. 2015.
Serra et al., "Pluripotent Stem Cell Differentiation Reveals Distinct Developmental Pathways Regulating Lung-versus Thyroid-Lineage Specification," *Development 144*: 3879-3893, 2017.
Xing et al., "The Impact of PM2.5 on the Human Respiratory System," *J Thorac Dis. 8.1*: E69-E74, Jan. 2016.
Zwozdziak et al., "Influence of PM1 and PM2.5 on Lung Function Parameters in Healthy Schoolchildren—A Panel Study," *Environ Sci Pollut Res. 23*: 23892-23901, Sep. 2016.

\* cited by examiner

METHOD FOR FABRICATION OF THREE-DIMENSIONAL LUNG ORGANOID COMPRISING HUMAN STEM CELL-DERIVED ALVEOLAR MACROPHAGE

CROSS-REFERENCES TO RELATED APPLICATION

This is the U.S. National Stage of International Application No. PCT/KR2019/018219, filed Dec. 20, 2019, which in turn claims the benefit of priority from Korean Patent Application No. 10-2018-0166267, filed on Dec. 20, 2018, the contents of each of which are incorporated herein by reference.

BACKGROUND OF THE INVENTION

1. Field of the Invention

The present invention relates to a method for fabrication of a three-dimensional lung organoid comprising human stem cell-derived alveolar macrophages.

2. Description of the Related Art

Recently, as fine dust has emerged as an important environmental issue that threatens the safety and health of the people, the level of fine dust pollution is continuously increasing, and the sensory index thereof is getting higher. Fine dust is classified into PM10 with a diameter of 10 μm or less, PM5 with a diameter of 5 μm or less, PM2.5 with a diameter of 2.5 μm or less, and PM1 with a diameter of 1 μm or less, depending on the particle size. Fine dust with a diameter of 2.5 μm or less is called 'ultra-fine dust'.

According to recent studies, chronic obstructive pulmonary disease (COPD), lung inflammation, emphysema, airway remodeling and the like have been reported in the rat model exposed to fine dust. In particular, studies have been continuously reported to confirm that the pulmonary function of people exposed to ultra-fine dust for a long time has decreased (Fang He et al., Scientific Report, 7:45666, 2017; Mary B. Rice et al., All AJRCCM, 191 (6): 656-664, 2015; Zwozdziak et al., Environ Sci Pollut Res Int, 23 (23): 23892-23901, 2016; and Yu-Fei Xing et al., J Thorac Dis, 1: E69-E74, 2016). Currently, researches on fine dust measuring equipment development, filter development, and fine dust reduction technology have been conducted, but development of a human risk assessment method of fine dust and researches on pathological mechanisms are insufficient.

In addition, humidifier disinfectants which were began to have reports of damage cases caused by them since the early 2000s and have been banned since 2012, were reported to cause lung injury with unknown cause. As a result of epidemiological investigation by the Disease Control and Prevention Agency, it was confirmed that patients with severe pulmonary disease with unknown cause due to humidifier disinfectants exhibit characteristics such as necrotizing bronchiolitis, rapidly progressing refractory hypoxia, and no response to steroids and immunosuppressants. There were also more than 4,800 low-stage victims who were not found to have such severe pulmonary disease. It is still reported that many patients suffer from humidifier disinfectants. However, the mechanism of lung fibrosis in humidifier disinfectant victims has been studied using animal models, but no clear treatment has been developed until now.

Treatment and management of pulmonary disease patients are required based on the accurate pulmonary disease diagnosis for the patients exposed to environmentally harmful factors such as fine dust and humidifier disinfectants. For this, it is necessary to evaluate pulmonary disease based on imaging, develop diagnostic technology, and discover markers through research on pathogenesis of pulmonary disease. Currently, animal models are mainly used as the lung fibrosis model, but due to the differences in physiological characteristics between humans and animals, immune responses and pharmacological results of drugs may be different from those of humans. Therefore, there are restrictions on the exact pathogenesis studies.

For research using cells, studies using the human primary cultured lung cells exposed to environmentally harmful factors are most ideal. However, since it is difficult to secure human primary cultured lung tissues or cells, and long-term culture is also difficult, studies are being conducted using immortalized cell lines. But, these cell lines do not accurately reflect the physiological characteristics of primary cultured cells, have a remarkably low rate of maintaining a normal karyotype, and consist of one type of cell. Therefore, there is a limitation in that they cannot accurately reflect the characteristics of the human lung tissue in which various cells maintain a three-dimensional shape.

On the other hand, organoids are organ-specific cell aggregates made by culturing three dimensionally, aggregating or recombinating stem cells, are capable of self-renewal and are also called 'mini organs' or 'similar organs'. Organoid is very useful for basic research because it has a form similar to an actual organ and can implement in vitro studies that are difficult to implement in animal models such as molecular signal regulation. In addition, it can be very useful in various fields such as human development, disease model establishment, drug efficacy evaluation screening, drug toxicity evaluation platform development, and cell therapy development.

Currently, studies for establishing various organoids have been conducted, and lung organoids have also been developed. As the prior arts related to the method for preparing a lung organoid, there are the following documents that disclose a method for preparing a lung organoid from hPSC: Development, 144:986-997, 2017 and Nature cell biology, 19 (5): 542-549, 2017.

However, the pulmonary organoids known to date do not contain alveolar macrophages, so there is a limitation in implementing infection or inflammatory reactions. Alveolar macrophages are macrophages present in the alveoli and have been reported to differentiate from yolk sac, not bone marrow. In fact, alveolar macrophages are significantly different from bone marrow-derived macrophages, and the markers of human alveolar macrophages are different from those of bone marrow-derived macrophages. If alveolar macrophages are not present in the lung organoid culture system, it is difficult to implement infection or inflammatory reactions. In order to overcome these limitations, a method of producing cells similar to human alveolar macrophages, and a method of inducing maturation into cells similar to alveolar macrophages by transplanting differentiated macrophages into humanized mouse lung tissue in vitro has been disclosed (Happle, C., et al. (2017). Induced pluripotent stem cell derived macrophages differentiate into AM like cells in the lungs of humanized PAP mice. Paediatric Bronchology.). However, there is no known method for preparing lung organoids comprising mature human alveolar macrophages.

Accordingly, the present inventors overlaid hPSCs on Matrigel® matrix and differentiated thereof by 2D method, and discovered that the lung organoid including alveolar macrophages can be prepared only when the mesoendoderm that does not express CXCR4 on days 4 to 5 of differentiation, resulting in the completion of the present invention.

SUMMARY OF THE INVENTION

It is an object of the present invention to provide a method for fabrication of a lung organoid comprising alveolar macrophages and a lung organoid prepared by the method.

To achieve the above object, the present invention provides a method for fabrication of a lung organoid comprising alveolar macrophages comprising the following steps:

1) differentiating stem cells to include definitive endoderm (DE) cells and mesoendoderm cells;
2) culturing the definitive endoderm cells and mesoendoderm cells of step 1) in a two-dimensional culture vessel to differentiate into anterior foregut endoderm (AFE) cells;
3) culturing the AFE cells of step 2) in a two-dimensional culture vessel; and
4) culturing the cultured cells of step 3) in a three-dimensional culture vessel.

In addition, the present invention provides a lung organoid comprising alveolar macrophages prepared by the method for fabrication of a lung organoid.

Advantageous Effect

The lung organoid prepared according to the preparation method of the present invention by differentiating cells that do not express CRCX4, a marker of complete endoderm cells, together includes type 1 and type 2 alveolar epithelial cells and at the same time alveolar macrophages. Therefore, the organoid can implement infection or inflammatory reactions unlike the existing lung organoids that do not contain immune cells, so it can be effectively used for research on the mechanism of related pulmonary disease, discovery of biomarkers, and development of therapeutic agents.

SEQUENCE

Figure 1A:
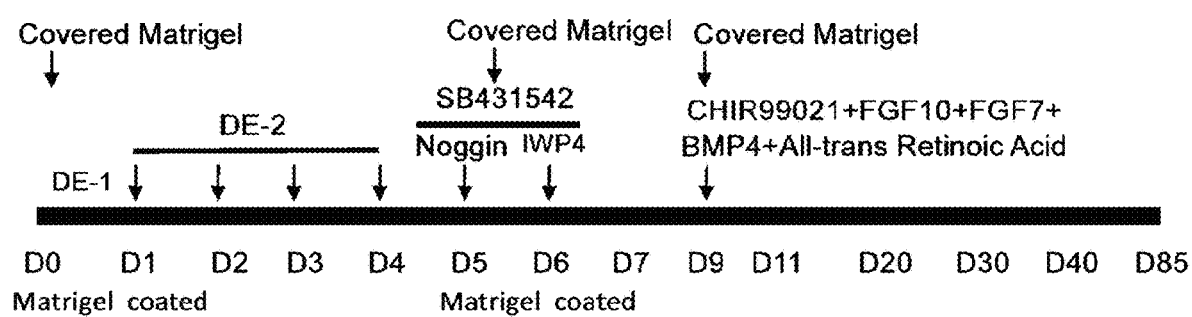
FIG. 1a is a schematic diagram showing the method for fabrication of a lung organoid according to the differentiation period from human pluripotent stem cells.

The Sequence Listing is submitted as an ASCII text file in the form of the file name "Sequence.txt" (~3 kb), which was created on Mar. 29, 2021, and which is incorporated by reference herein.

DESCRIPTION OF THE PREFERRED EMBODIMENTS

Hereinafter, the present invention is described in detail.

The present invention provides a method for fabrication of a lung organoid comprising alveolar macrophages comprising the following steps:
1) differentiating stem cells to include definitive endoderm (DE) cells and mesoendoderm cells;
2) culturing the definitive endoderm cells and mesoendoderm cells of step 1) in a two-dimensional culture vessel to differentiate into anterior foregut endoderm (AFE) cells;
3) culturing the AFE cells of step 2) in a two-dimensional culture vessel; and
4) culturing the cultured cells of step 3) in a three-dimensional culture vessel.

The stem cells can be embryonic stem cells, induced pluripotent stem cells, or adult stem cells, and can be derived from humans, but not always limited thereto.

The definitive endoderm cells can be contained in a proportion of 50 to 90% of the total cells, particularly 50 to 80%, and more particularly 70 to 80%.

The mesoendoderm cells can be contained in a proportion of 10 to 40% of the cells do not express CXCR4, a marker of definitive endoderm cells, particularly 10 to 30%, and more particularly 15 to 25%.

The differentiation may be to differentiate stem cells in a Matrigel®-matrix coated culture vessel to simulate the microenvironment of cells, but not always limited thereto. At this time, fibronectin or laminin-coated culture vessels can be used.

The differentiation of step 1) can be performed for 2 to 6 days, preferably for 3 to 6 days, or more preferably for 4 to 6 days.

The culture of step 2) is performed in an anteriorization medium.

The anteriorization medium contains a TGF-β (transforming growth factor beta) signaling pathway inhibitor and a Wnt signaling pathway inhibitor, and the cells can be differentiated into anterior foregut endoderm cells using them.

Particularly, the TGF-β signaling pathway inhibitor can be SB431542 and Noggin, and the Wnt signaling pathway inhibitor can be IWP-2, IWP-3, or IWP-4, but not always limited thereto.

The said SB431542 is represented by the following formula, and can be included in the medium at the concentrations of 8 to 20 µM, preferably 8 to 15 µM, or more preferably 5 to 15 µM.

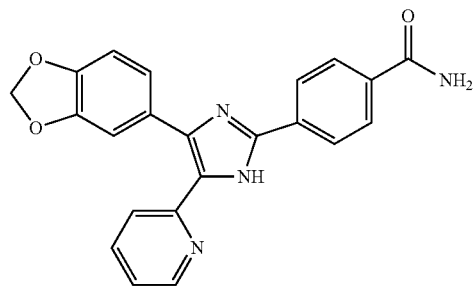 [SMILES: NC(=O)c1ccc(-c2nc(-c3ccc4c(c3)OCO4)c(-c3ccccn3)[nH]2)cc1]

The said Noggin can be included in the medium at the concentrations of 50 to 150 ng/ml, preferably 80 to 150 ng/ml, or more preferably 80 to 120 ng/ml.

The said IWP-2 (inhibitor of Wnt production-2), IWP-3 (inhibitor of Wnt production-3) or IWP-4 (inhibitor of Wnt production-4) can be included in the medium at the concentrations of 0.2 to 2 µM, preferably 0.5 to 2 µM, or more preferably 0.8 to 2 µM.

The culture of step 3) is performed in a LO (lung organoid formation) medium containing Matrigel® matrix.

In addition, the LO medium contains a GSK-3β (glycogen synthase kinase 3 beta) inhibitor, a fibroblast growth factor (FGF), a lung branched-type proliferation inhibitor, and an alveolar regeneration activator. Particularly, the GSK-3β inhibitor can be CHIR 99021, the fibroblast growth factor can be FGF10 or FGF7/KGF (keratinocyte growth factor), the lung branched-type proliferation inhibitor can be a bone morphogenetic protein (BMP), the alveolar regeneration activator can be all-trans retinoic acid, and the bone morphogenetic protein can be BMP4, but not always limited thereto.

The said CHIR 99021 is represented by the following formula, and can be included in the medium at the concentrations of 0.5 to 10 µM, preferably 0.8 to 10 UM, or more preferably 1.5 to 10 µM.

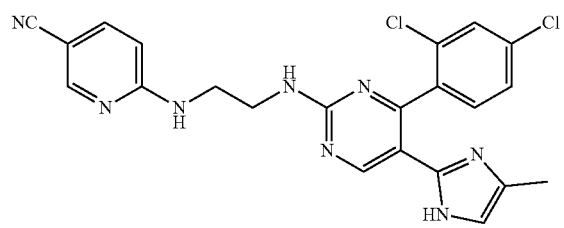 [SMILES: Cc1c[nH]c(-c2cnc(NCCNc3ccc(C#N)cn3)nc2-c2ccc(Cl)cc2Cl)n1]

The said FGF10 (fibroblast growth factor 10) can be included in the medium at the concentrations of 8 to 20 µM, preferably 8 to 15 µM, or more preferably 5 to 15 µM.

The said FGF7/KGF (fibroblast growth factor 7/keratinocyte growth factor) can be included in the medium at the concentrations of 8 to 20 ng/ml, preferably 8 to 15 ng/ml, or more preferably 5 to 15 ng/ml.

The said BMP4 (bone morphogenetic protein 4) can be included in the medium at the concentrations of 8 to 20 ng/ml, preferably 8 to 15 ng/ml, or more preferably 5 to 15 ng/ml.

The said all-trans retinoic acid can be included in the medium at the concentrations of 20 to 80 nM, preferably 30 to 80 nM, or more preferably 40 to 80 nM.

The culture of step 4) is performed in a LO (lung organoid formation) medium not containing Matrigel®matrix.

The culture in a two-dimensional culture vessel of step 2) can be performed starting from the 3$^{rd}$ to 7$^{th}$ day of the differentiation, preferably from the 4$^{th}$ to 6$^{th}$ day of the differentiation, and more preferably from the 4$^{th}$ to 5$^{th}$ day of the differentiation for 1 to 7 days, 1 to 5 days, or 1 to 4 days.

The culture in a two-dimensional culture vessel of step 3) can be performed starting from the 5$^{th}$ to 15$^{th}$ day of the differentiation, preferably from the 6$^{th}$ to 12$^{th}$ day of the differentiation, and more preferably from the 7$^{th}$ to 10th day of the differentiation for 5 to 20 days, 7 to 15 days, or 10 to 14 days.

The culture in a three-dimensional culture vessel can be performed starting from the 15$^{th}$ to 25$^{th}$ day of the differentiation, preferably from the 18$^{th}$ to 23$^{rd}$ day of the differentiation, and more preferably from the 19$^{th}$ to 21$^{st}$ day of the differentiation for 10 days to 1 year, 15 days to 6 months, or 20 days to 30 days.

In addition, the present invention provides a lung organoid comprising alveolar macrophages prepared by the method for fabrication of a lung organoid.

In a preferred embodiment of the present invention, the present inventors differentiated human pluripotent stem cells (hPSCs) to include DE cells and mesoendoderm cells, and then differentiated them into AFE cells using an anteriorization medium containing Matrigel® matrix in a Matrigel®-matrix coated culture vessel. On the 20$^{th}$ day of the differentiation, the cells were transferred to a three-dimensional culture vessel and cultured using a LO medium not containing Matrigel® matrix. As a result, a lung organoid was prepared (see FIG. 1a).

The lung organoid prepared from the cells cultured after changing to 3-D culture on the 20$^{th}$ day of the differentiation formed a three-dimensional spherical shape, compared to a cluster-shaped cell aggregate otherwise. Therefore, it was confirmed that the three-dimensional culture is absolutely necessary. (see FIGS. 1b and 1c).

Figure 2A:
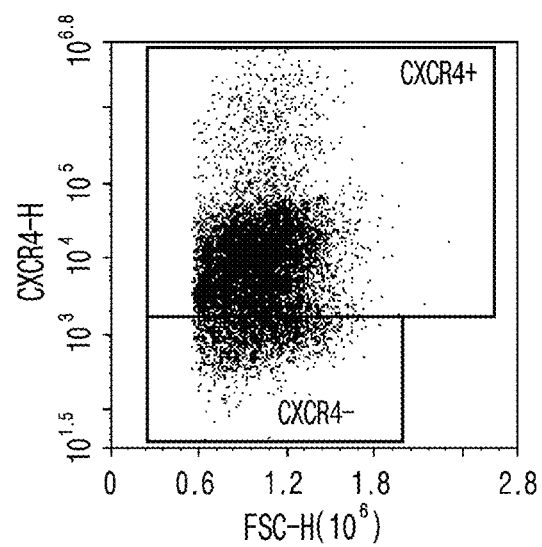
FIG. 2a is a diagram showing the results of flow cytometry (FACS) of differentiated cell markers on the fourth day of the differentiation, and confirming that 20 to 30% of total cells are CXCR4 negative cells.
Figure 2B:
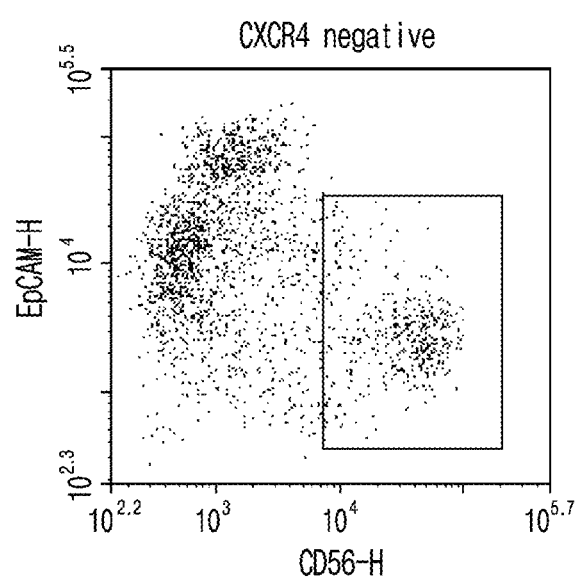
FIG. 2b is a diagram showing the results of flow cytometry (FACS) of differentiated cell markers on the fourth day of the differentiation, and confirming that EpCAM and CD56, the markers of mesoendoderm cells, were expressed in 20.99% of CXCR4 negative cells.

In addition, the present inventors confirmed that the lung organoid comprising alveolar macrophages can be prepared only when the cells expressing EpCAM (−) CD56 (+), a mesoendoderm cell marker, should be included in a proportion of about 20% of the cells not expressing CXCR4, after culturing stem cells until the cells expressing CXCR4, a definitive endoderm cell marker, occupied a proportion of 70 to 80 (see FIGS. 2a and 2b).

Figure 3:
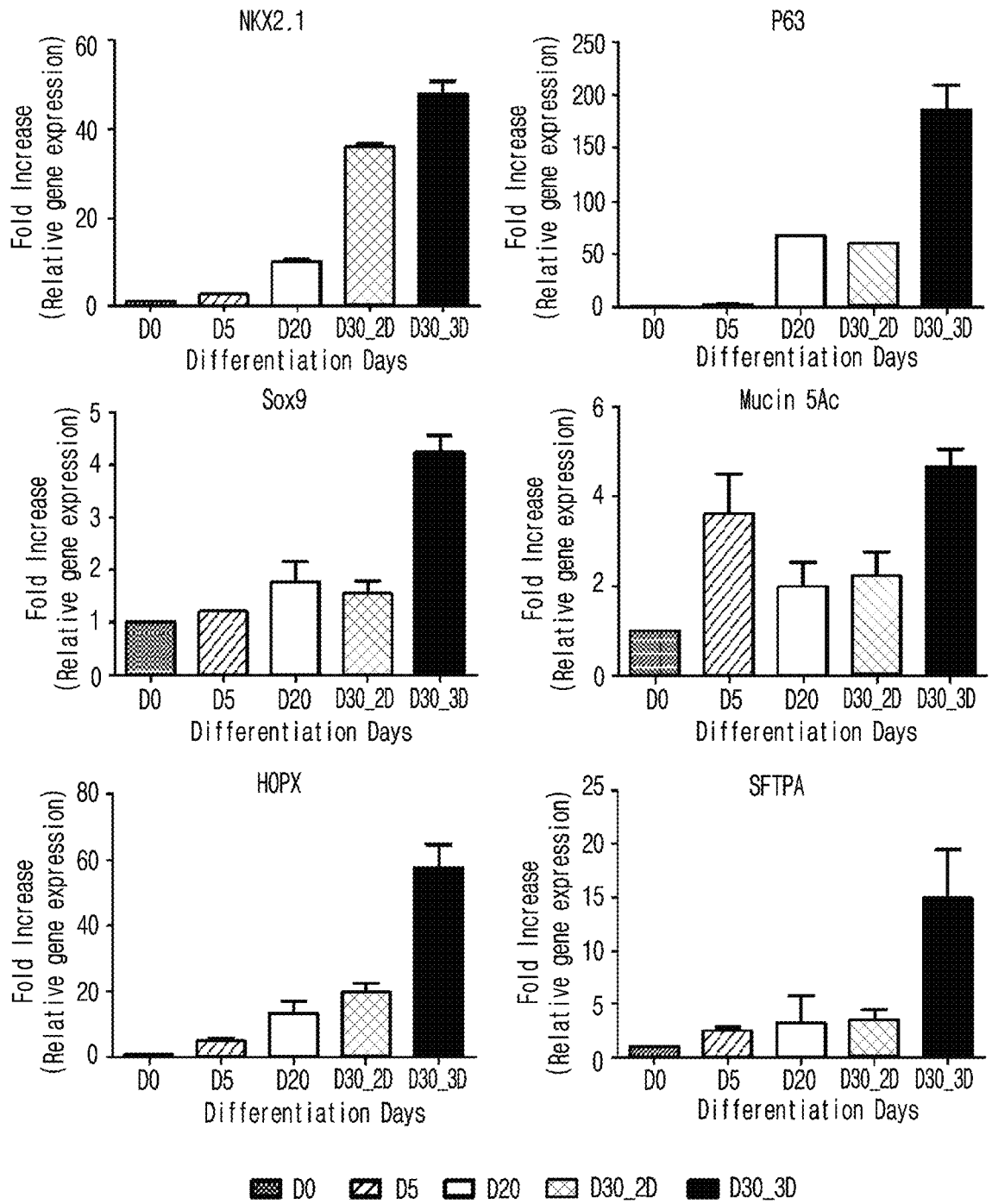
FIG. 3 is a graph showing the results of quantitative polymerase chain reaction (qPCR) measuring the expression level of alveolar cell-specific genes according to the differentiation period and the presence or absence of 3D culture.
Figure 4A:
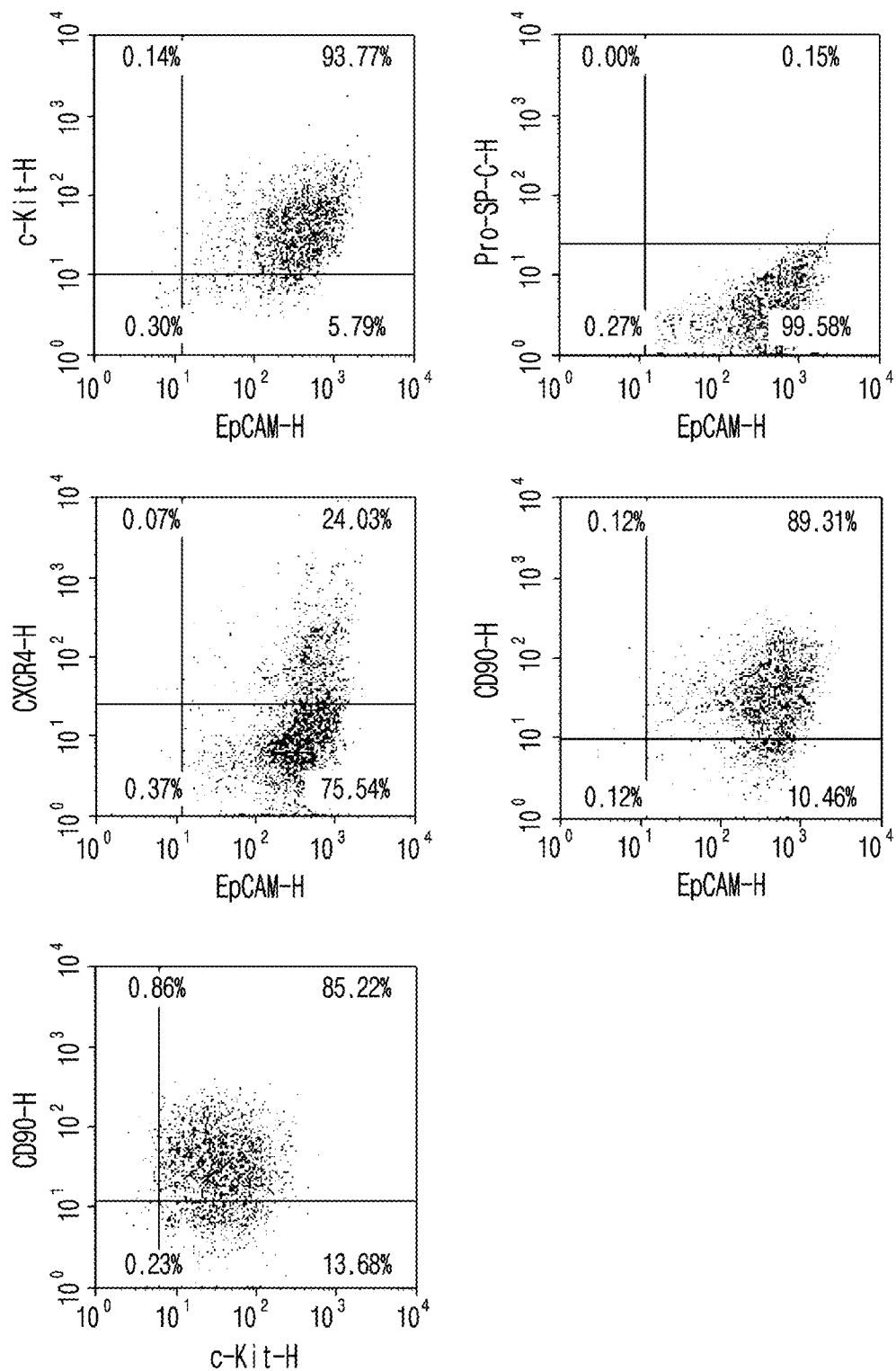
FIG. 4a is a graph showing the results of fluorescence-activated cell sorting (FACS) measuring the expression level of alveolar cell-specific genes (EpCAM, c-Kit, CXCR4, Pro-surfactant protein C and CD90) on the $10^{th}$ day of the differentiation.
Figure 4B:
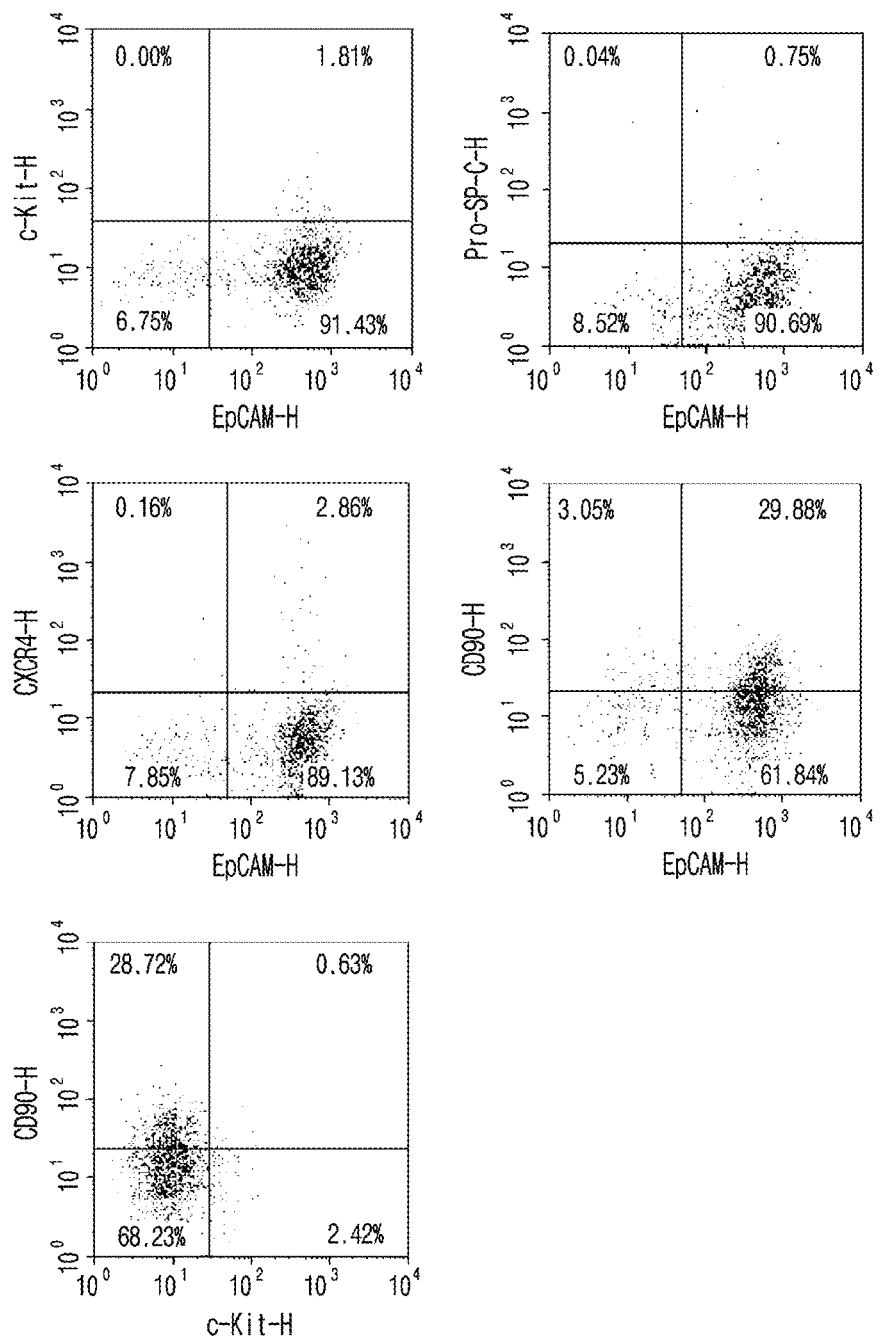
FIG. 4b is a graph showing the results of fluorescence-activated cell sorting (FACS) measuring the expression level of alveolar cell-specific genes (EpCAM, c-Kit, CXCR4, Pro-surfactant protein C and CD90) on the $20^{th}$ day of the differentiation.
Figure 4C:
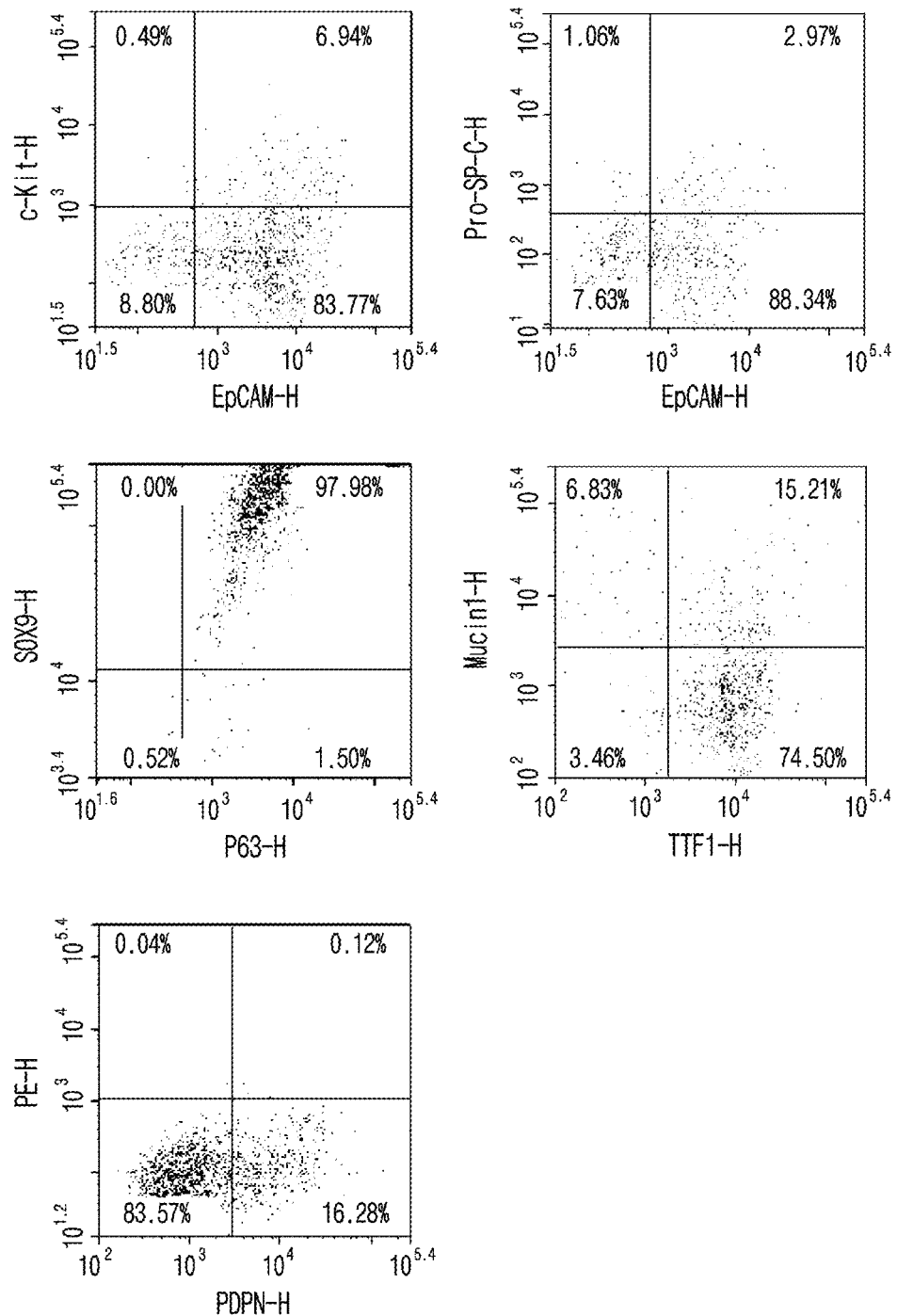
FIG. 4c is a graph showing the results of fluorescence-activated cell sorting (FACS) measuring the expression level of alveolar cell-specific genes (EpCAM, c-Kit, CXCR4, Pro-surfactant protein C and CD90) on the $30^{th}$ day of the differentiation.
Figure 4D:
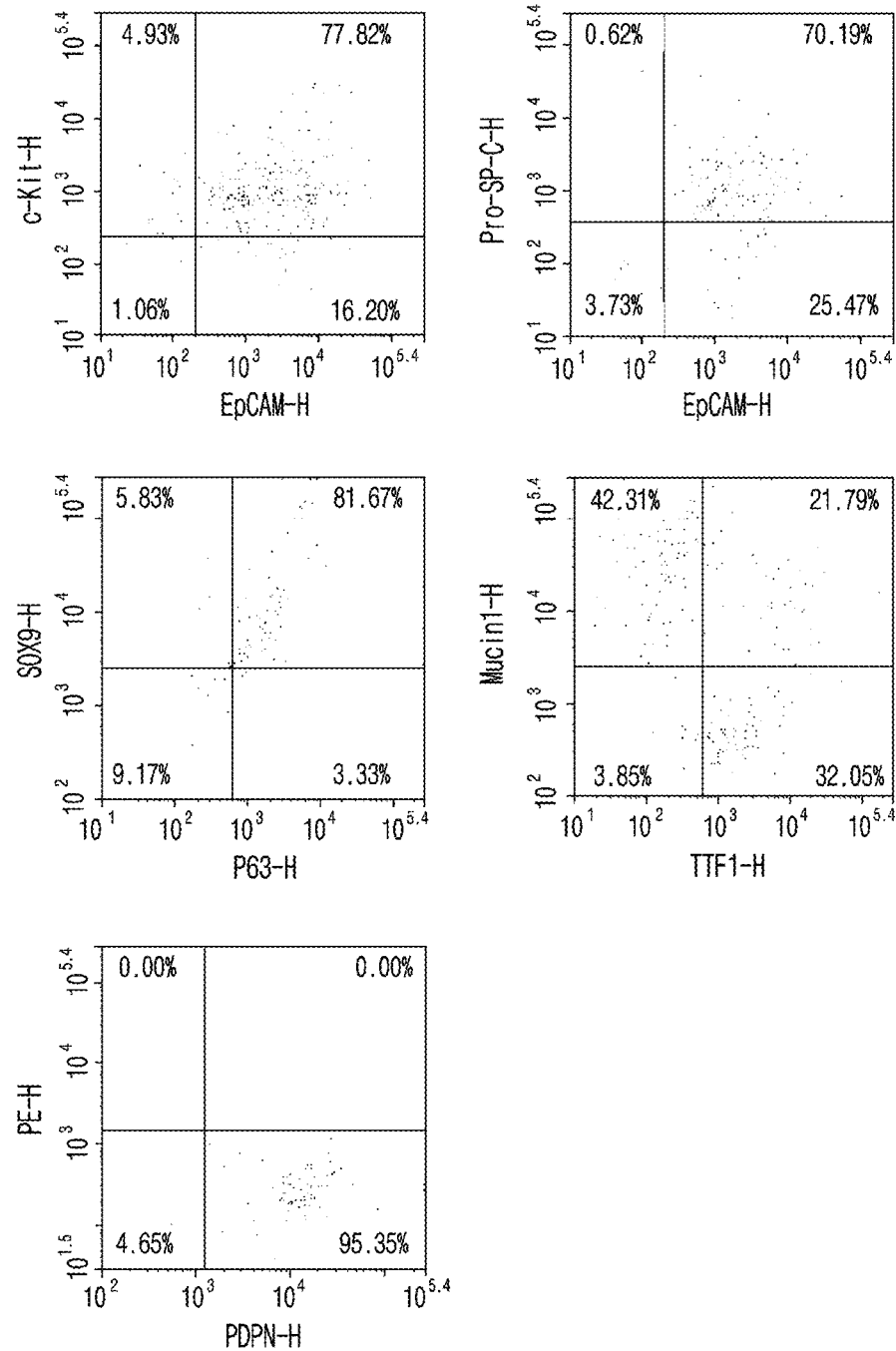
FIG. 4d is a graph showing the results of fluorescence-activated cell sorting (FACS) measuring the expression level of alveolar cell-specific genes (EpCAM, c-Kit, CXCR4, Pro-surfactant protein C and CD90) of the cells changed to 3D culture on the $20^{th}$ day of the differentiation.

The present inventors also confirmed that the expression of the lung tissue-specific gene was highest in the lung organoid prepared from the cells cultured after changing to 3-D culture on the 20$^{th}$ day of the differentiation (see FIG. 3).

The present inventors also confirmed that the alveolar epithelial cell markers (type 1 and type 2 alveolar epithelial cell markers) were expressed in the lung organoid on the 30$^{th}$ day of the differentiation (see FIGS. 4a to 4d).

Figure 5A:
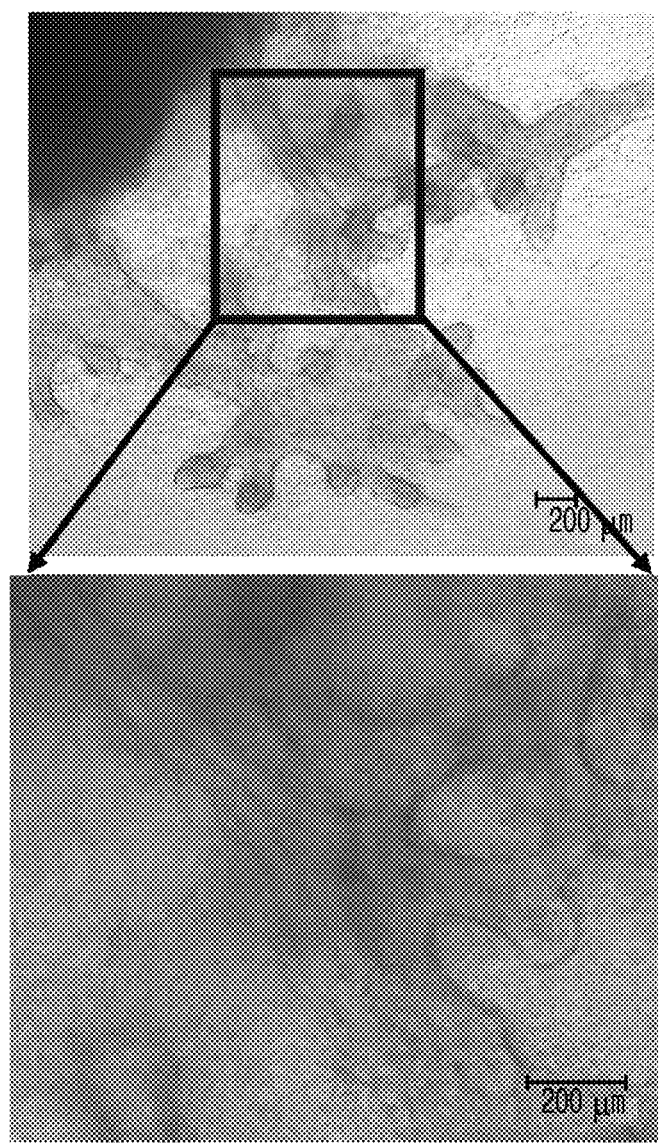
FIG. 5a is a photograph showing the alveolar structure including a branch structure of a three-dimensional lung organoid.
Figure 5B:
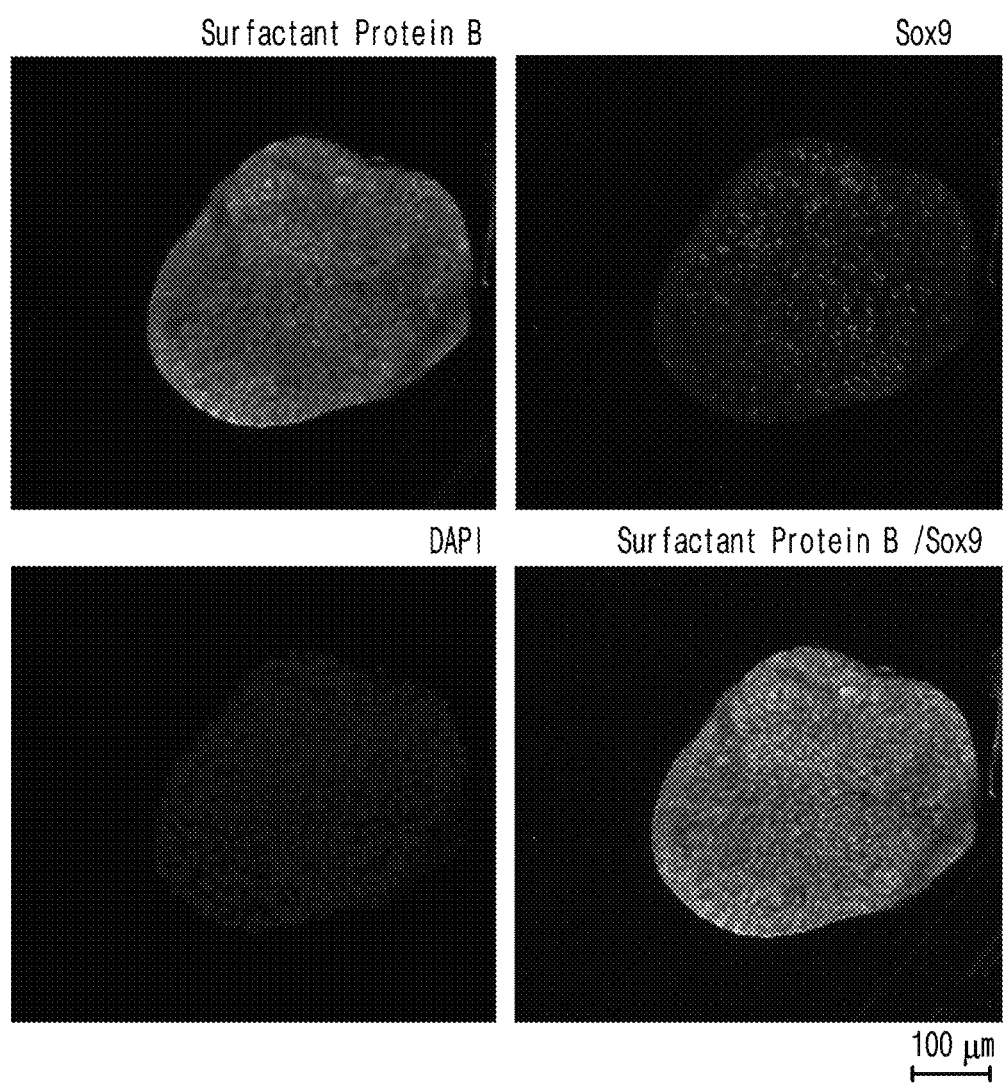
FIG. 5b is a photograph showing the honeycomb structure of a cross section of a branch structure of a three-dimensional lung organoid.

The present inventors also confirmed that the prepared lung organoid formed a branched structure like a human lung shape, formed an alveolar shape (FIG. 5a), and had a honeycomb-like structure surrounded by cells forming a thin membrane similar to the structure of human alveoli (FIG. 5b). The present inventors observed that the alveolar cell-specific protein was expressed (FIG. 5C) and the alveolar-specific lamellar body was formed (FIG. 5d) in the prepared lung organoid.

Figure 6A:
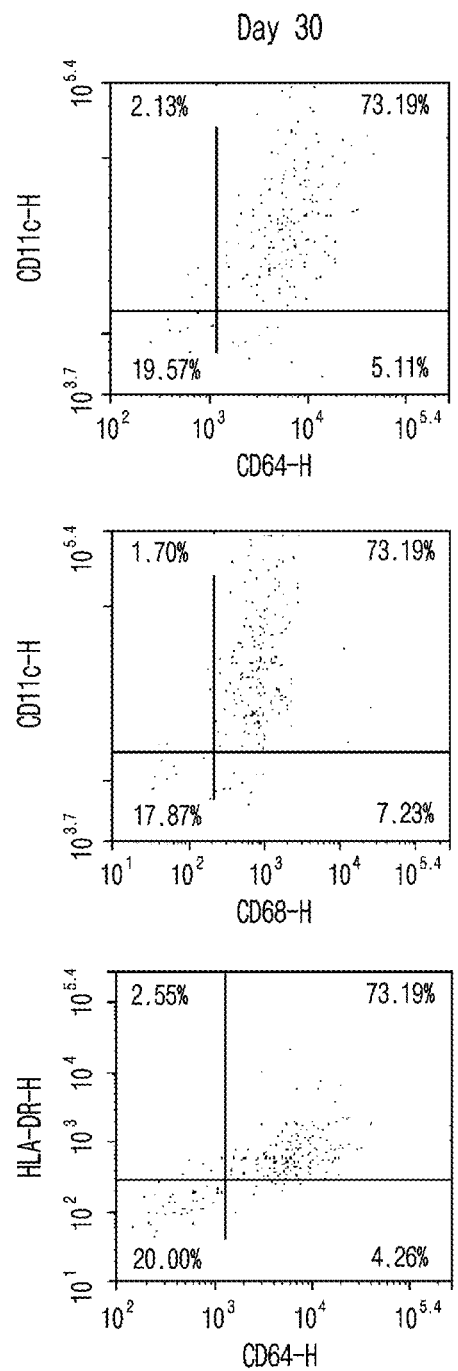
FIG. 6a is a graph showing the results of FACS confirming the expression of an alveolar macrophage-specific protein on the $30^{th}$ day of the differentiation of a three-dimensional lung organoid.
Figure 6B:
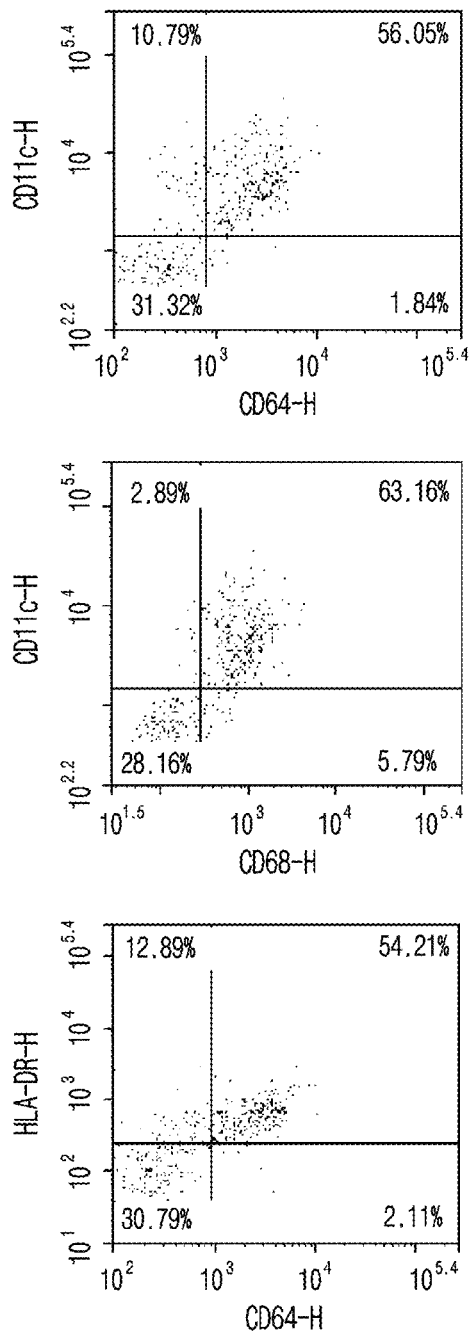
FIG. 6b is a graph showing the results of FACS confirming the expression of an alveolar macrophage-specific protein on the $60^{th}$ day of the differentiation.
Figure 6C:
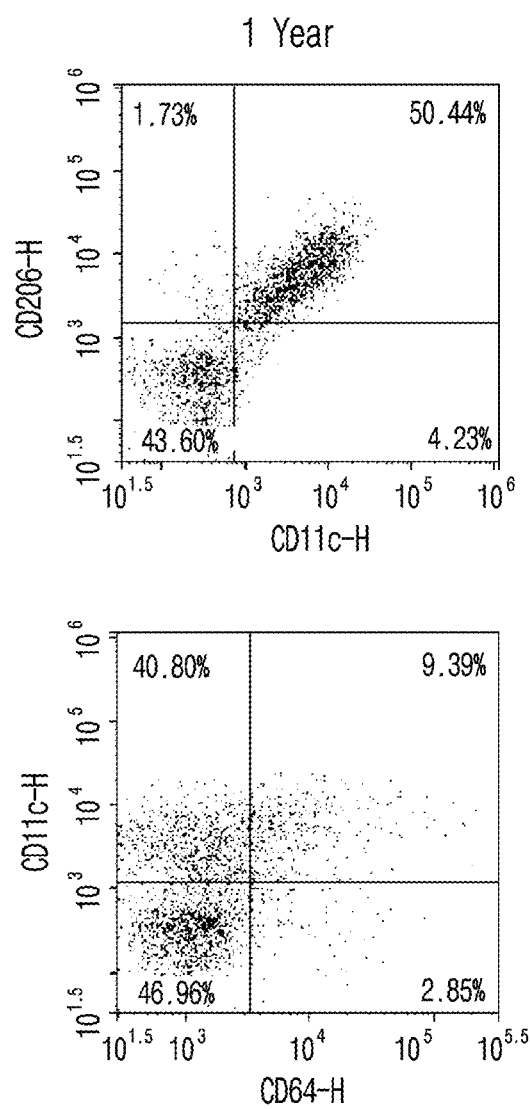
FIG. 6c is a graph showing the results of FACS confirming the expression of an alveolar macrophage-specific protein 1 year after the differentiation.

The present inventors also confirmed that alveolar macrophages existed in the prepared lung organoids by confirming that the alveolar macrophage-specific markers were expressed in the lung organoids on the 30$^{th}$ day, 60$^{th}$ day and 1 year of the differentiation (FIGS. 6a to 6c).

Figure 7A:
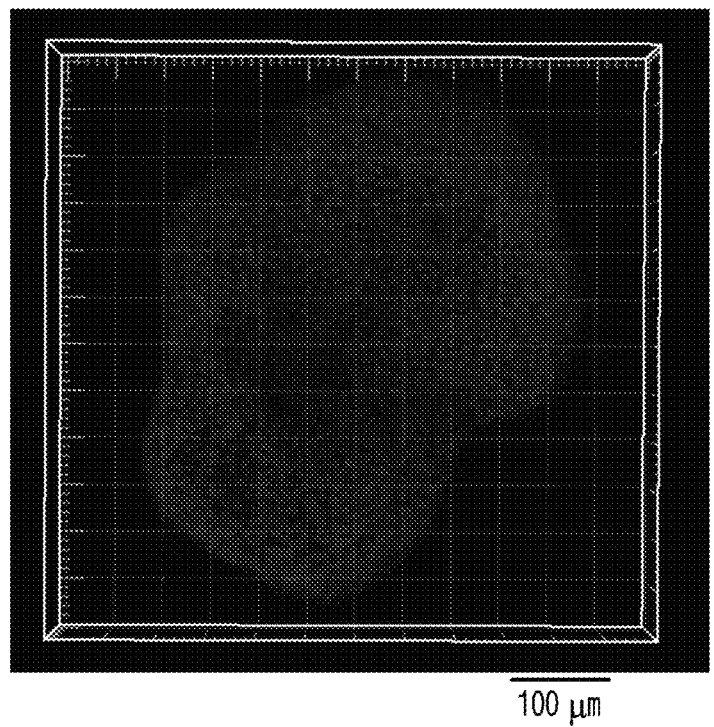
FIG. 7a is a photograph confirming that there is no nonspecific reaction of the antibody used using only the secondary antibody without the primary antibody.
Figure 7B:
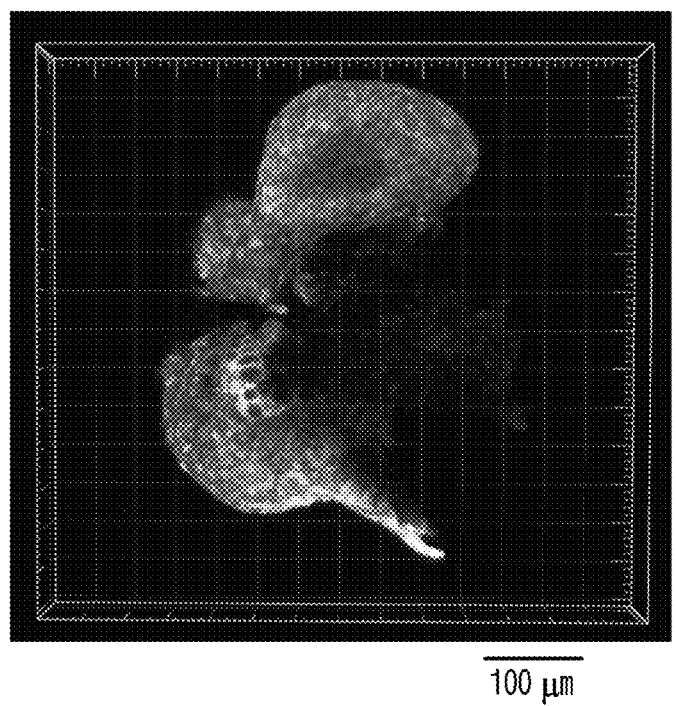
FIG. 7b is a photograph showing the stained pro-surfactant protein C, a type 2 alveolar cell marker.
Figure 7C:
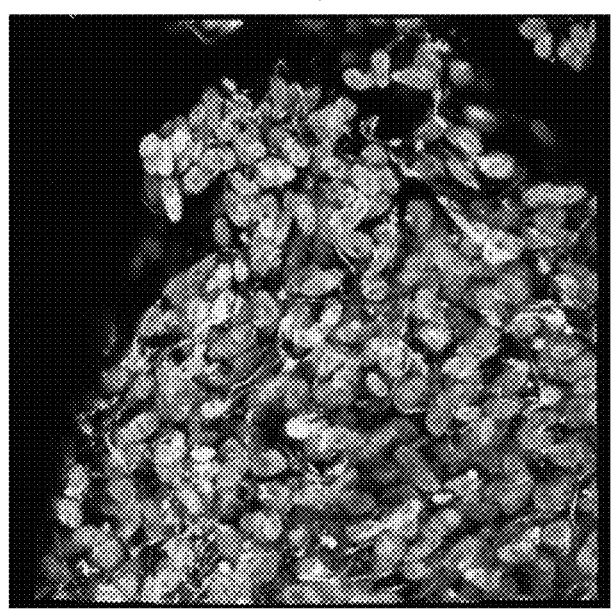
FIG. 7c is a photograph showing the stained PDPN, a type 1 alveolar cell marker.
Figure 7D:
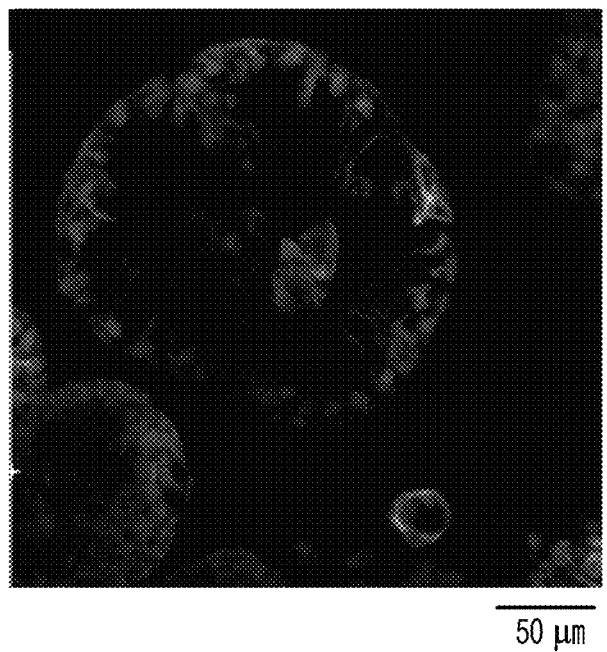
FIG. 7d is a photograph showing the stained CD68, an alveolar macrophage marker.

The present inventors also confirmed that the lung organoid of the present invention contained alveolar macrophages as well as type 1 and type 2 alveolar epithelial cells by confirming that pro-surfactant protein c (type 2 alveolar epithelial cell marker) (FIG. 7b), PDPN (type 1 alveolar epithelial cell marker) (FIG. 7c) and CD68 (alveolar macrophage marker) (FIG. 7d) were expressed in the lung organoid on the 70$^{th}$ day of the differentiation.

Figure 8A:
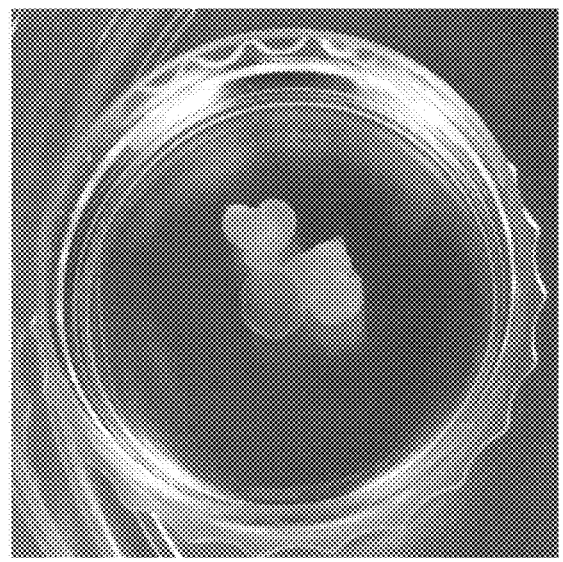
FIG. 8a is a photograph showing the appearance of a three-dimensional lung organoid 10 months after the differentiation.
Figure 8B:
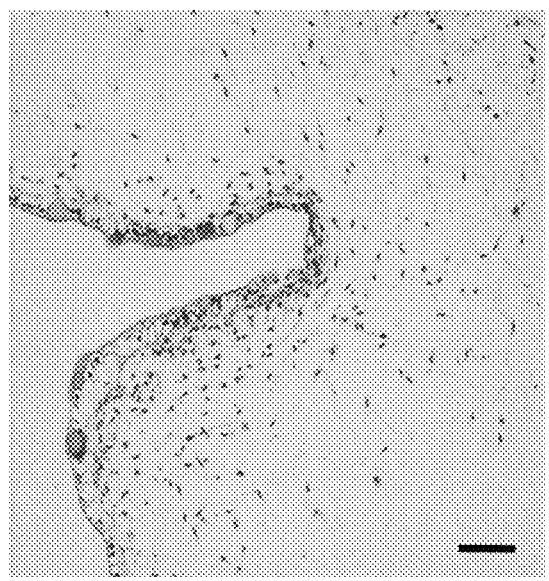
FIG. 8b is a photograph showing the three-dimensional lung organoid stained with H&E 10 months after the differentiation.
Figure 9:
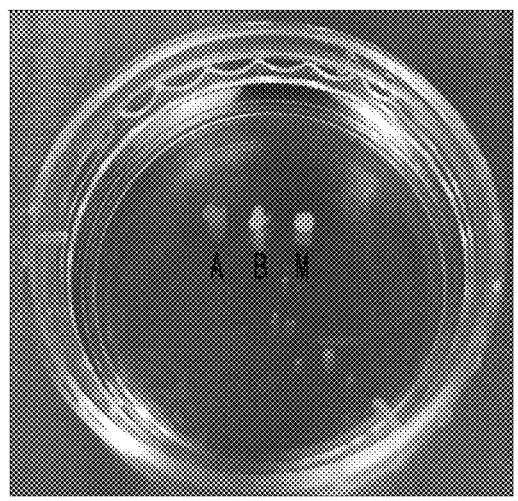
FIG. 9 is a photograph showing the A-type, B-type and M-type morphology of a three-dimensional lung organoid on the $85^{th}$ day of the differentiation.

The present inventors also confirmed that the epithelial cells that form a thin film and a lumen surrounded by a thin film similar to the human alveolar structure existed in the lung organoid on the 10th month of the differentiation (see FIGS. 8a and 8b).

Figure 10A:
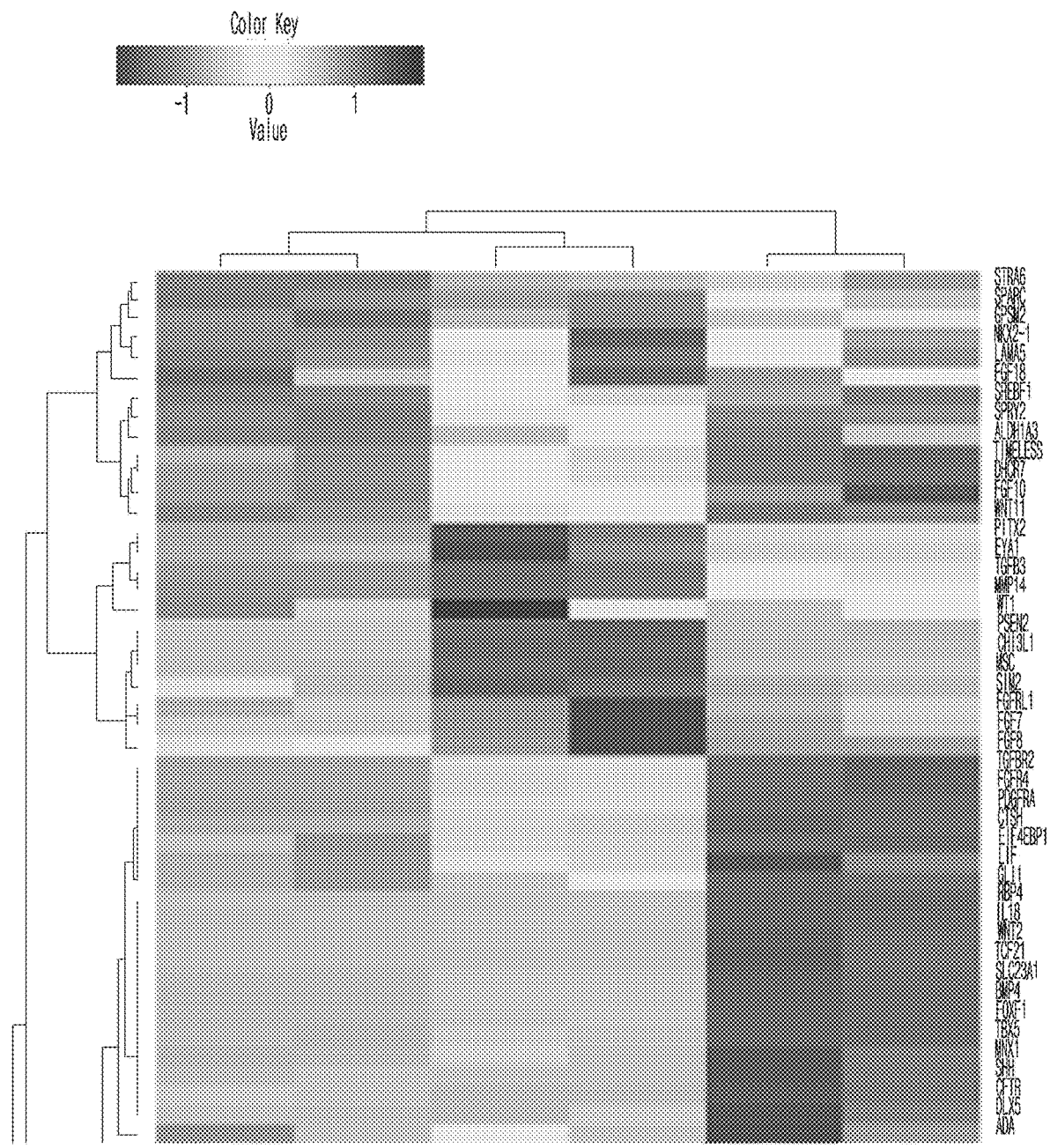
FIGS. 10a and 10b show a diagram showing the results of RNA sequencing of genes related to respiratory system development according to the A type, B type and M type morphology of a three-dimensional lung organoid on the $85^{th}$ day of the differentiation.
Figure 10B:
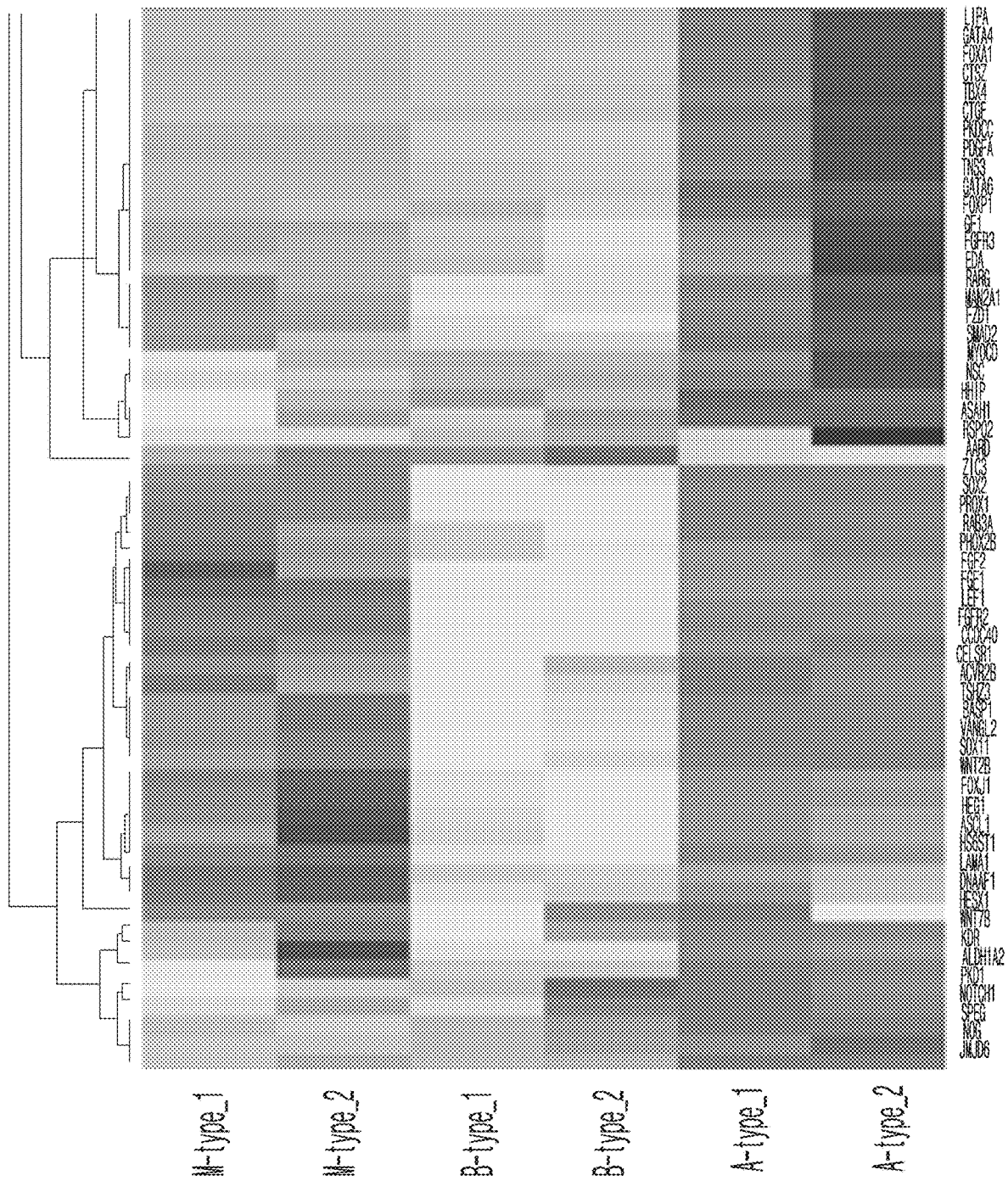
Figure 10C:
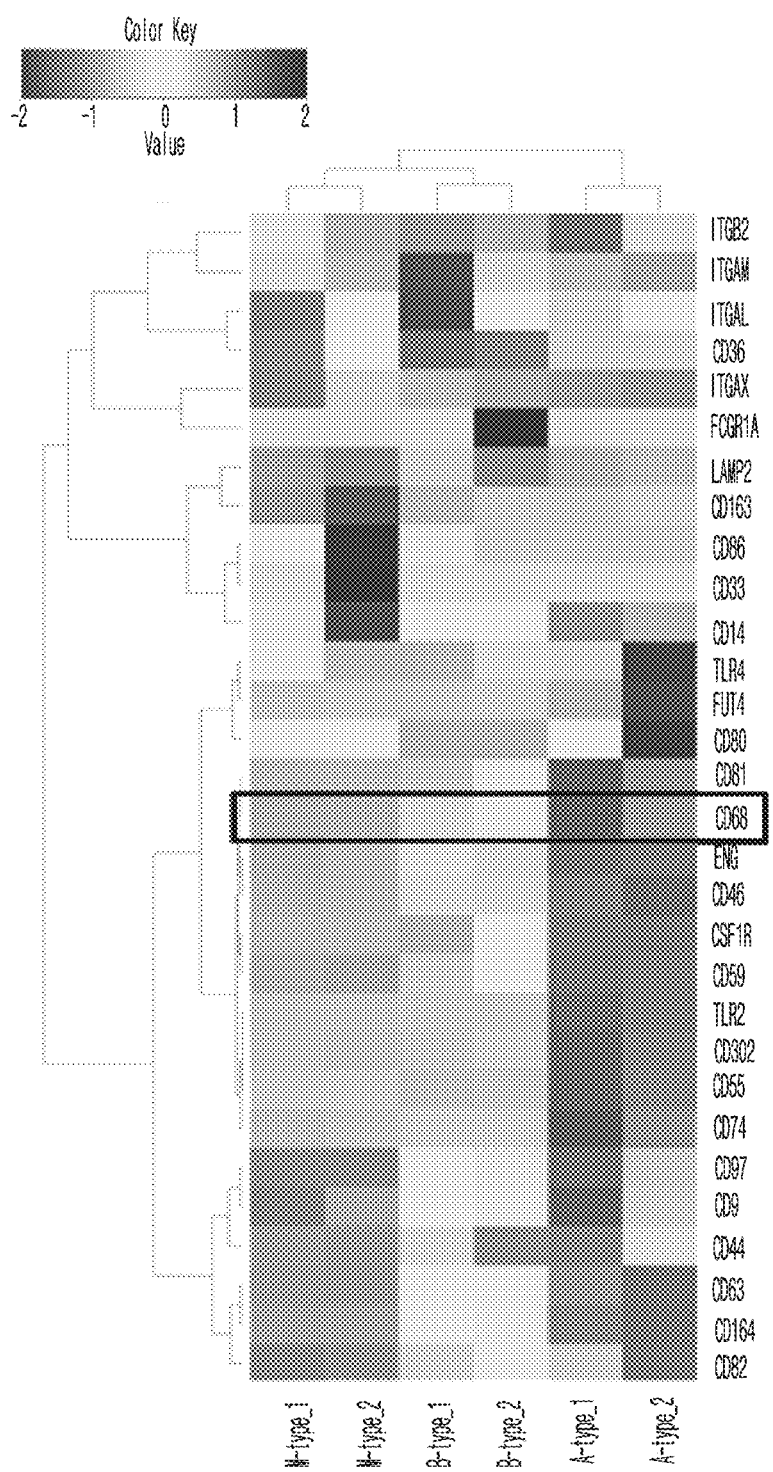
FIG. 10c is a diagram showing the results of RNA sequencing of macrophage-related genes according to the A-type, B-type and M-type morphology of a three-dimensional lung organoid on the 85th day of the differentiation, and confirming that the expression of macrophage-related gene (CD68) was strongly expressed in the lung organoid.

In addition, the present inventors confirmed that the prepared lung organoid contained alveolar macrophages by confirming the gene expression pattern according to the morphology of the prepared lung organoid and that the expression of the alveolar macrophage-related gene CD68 was strongly expressed in the A type lung organoid that showed a clear alveolar morphology (see FIGS. 10a, 10b, and 10c).

Therefore, the method for fabrication of a lung organoid comprising alveolar macrophages according to the present invention and the lung organoid prepared by the method can implement infection or inflammatory reactions unlike the existing lung organoids that do not contain immune cells, so they can be effectively used for research on the mechanism of related pulmonary disease, discovery of biomarkers, and development of therapeutic agents.

Hereinafter, the present invention will be described in detail by the following examples.

However, the following examples are only for illustrating the present invention, and the Contents of the Present Invention are not Limited Thereto.

Example 1: Preparation of Three-Dimensional Lung Organoid

<1-1> Plate Coating

The Matrigel® matrix (Matrigel®-hESC qualified Matrix, Cat. #. 354277, Corning, USA) that can simulate the extracellular microenvironment was diluted 200 times using cold DMEM/F12 medium (final Matrigel® matrix concentration: 250~290 µl/500 ml), and put in a 4-well plate (400 µl/well), followed by coating in a 37° C., 5% CO2 incubator for 1 hour.

<1-2> Day-1 of Differentiation

Each well of a cell culture plate were coated by adding 10 µg of Vitronectin XF (Cat. #. 07180, Stem cell technologies) to the plate. The human pluripotent stem cell line H9 (Wicell, WA09-FD) was prepared by culturing in the coated plate containing TeSR™-E8™ medium (Cat. #. 05940, Stem cell technologies) (2 ml/well) under conditions of 37° C. and 5% CO2. At this time, the medium was changed every day during the subculture period.

After removing the culture medium of the cultured H9 cells (WiCell, USA), 1 ml of 0.5 mM EDTA (Ethylenediaminetetraacetic acid) was added to each well of the plate, followed by reaction in a 37° C., 5% CO2 incubator for 5 to 7 minutes. Then, EDTA was removed and 1 ml of the stem cell culture medium (TeSR™-E8™ medium) supplemented with 10 µM ROCK (Rho-associated, coiled-coil containing protein kinase) inhibitor (Y-27632, Cat. #. 04-0012-02, Stemgent, USA) was added to each well, followed by pipetting to obtain cells. The obtained cells were counted, diluted in the mTeSR™-1 medium (Cat. #. 5850, STEMCELL Technologies, Canada) supplemented with 10 µM ROCK inhibitor and Matrigel® matrix (1:200), and seeded in the 6-well plate coated in Example <1-1> at the density of 1.25×10$^5$ cells/well to start culture.

<1-3> Day 0 of Differentiation

After removing the medium and washing with DPBS (Dulbecco's Phosphate-Buffered Saline), the DE-1 medium (DE basal medium) having the composition shown in Table 1 was added to the plate (2 ml/well), followed by culture for 24 hours.

TABLE 1

Composition of DE-1 medium (10 ml)

DMEM/F12 (9.597 ml)
1 × N2 supplement (Cat. #. 17502048, Gibco) (100 µl)
1 × B27 ™ supplement (Cat. #. 17504-044, Gibco) (200 µl)
1 × P/S (Penicillin/streptomycin) (Cat. #. 15140-122, Gibco) (100 µl)
50 ng/ml Activin A (Cat. #. 338-AC, R&D system, 100 µl/ml stock) (5 µl)
0.5 mM sodium butyrate (Cat. #. 303410, Sigma, 1M stock) (5 µl)
3 µM CHIR 99021 (Cat. #. S1263, Selleckchem, 10 mM stock) (3 µl)

<1-4> Day 1 to 3 or 4 of Differentiation: Differentiation of Stem Cells to Include Definitive Endoderm (DE) Cells and Mesoendoderm Cells After removing the medium, the DE-2 medium having the composition shown in Table 2 was added to the plate (2 ml/well), followed by culture for 24 hours. The medium was changed every 24 hours. On the 4$^{th}$ or 5$^{th}$ day from the start of differentiation, it was confirmed that the DE (definitive endoderm) marker CXCR4 was expressed in 70 to 80% of cells, and then the steps of Example <1-5> was carried out.

TABLE 2

Composition of DE-2 medium (10 ml)

DMEM/F12 (9.587 ml)
1 × N2 supplement (Cat. #. 17502048, Gibco) (100 µl)
1 × B27 ™ supplement (Cat. #. 17504-044, Gibco) (200 µl)
1 × P/S (Penicillin/streptomycin) (Cat. #. 15140-122, Gibco) (100 µl)
50 ng/ml Activin A (Cat. #. 338-AC, R&D system, 100 µl/ml stock) (5 µl)
0.5 mM sodium butyrate (Cat. #. 303410, Sigma, 1M stock) (1 µl)

<1-5> Day 4 or 5 of Differentiation: Differentiation of Definitive Endoderm (DE) Cells and Mesoendoderm Cells into Anterior Foregut Endoderm Cells After removing the medium and washing with DPBS, TrypLE™ Express (Gibco, Cat #: 12604013), a recombinant enzyme used for cell dissociation, was added thereto, followed by culture for 3 to 5 minutes. Then, TrypLE™ Express was removed, and the cells were collected by adding DPBS, followed by centrifugation at 1,300 rpm for 5 minutes. DPBS was removed, and 1 ml of the anteriorization-1 medium containing Matrigel® matrix (Table 3) was added to each well of the plate, followed by suspending. The cells were counted, diluted with the anteriorization-1 medium, seeded in a 6-well plate coated in Example <1-1> at the density of 5~9×10$^5$ cells/well, and cultured for 24 hours.

TABLE 3

Composition of anteriorization-1 medium (5 ml)

DMEM/F12 (4.790 ml)
1 × N2 supplement (Cat. #. 17502048, Gibco) (50 µl)
1 × B27 ™ supplement (Cat. #. 17504-044, Gibco) (100 µl)
1 × P/S (Penicillin/Streptomycin) (Cat. #. 15140-122, Gibco) (50 µl)
100 ng/ml Noggin (Cat. #. 120-10C, Peprotech, 100 µg/ml stock) (5 µl)
10 µM SB431542 (Cat. #. S1067, Selleckchem, 10 mM stock) (5 µl)
1/200 Matrigel ® matrix <1-6> Day 6 of Differentiation: Differentiation of Definitive Endoderm (DE) Cells and Mesoendoderm Cells into Anterior Foregut Endoderm Cells After removing the medium, the anteriorization-2 medium containing Matrigel® matrix (Table 4) was added to the plate (2 ml/well), followed by culture for 48 hours.

TABLE 4

Composition of anteriorization-2 medium (5 ml)

DMEM/F12 (4.8 ml)
1 × N2 supplement (Cat. #. 17502048, Gibco) (50 µl)
1 × B27 ™ supplement (Cat. #. 17504-044, Gibco) (100 µl)
1 × P/S (Penicillin/Streptomycin)(Cat. #. 15140-122, Gibco) (5 µl)

TABLE 4-continued

Composition of anteriorization-2 medium (5 ml)

1 µM IWP-4 (Cat. #. 04-0036, Stemgent, 1 mM stock) (5 µl)
10 µM SB431542 (Cat. #. S1067, Selleckchem, 10 mM stock) (5 µl)
1/200 Matrigel ® matrix <1-7> Day 8 to Day 20 of Differentiation After removing the medium, the lung organoid formation (LO) medium (Table 5) was added to the plate (2 ml/well), followed by culture. Every 2 days, half of the medium was replaced with a fresh medium.

TABLE 5

| Composition of LO medium (50 mℓ) |
| --- |
| DMEM/F12 (47.965 mℓ) |
| 1 × N2 supplement (Cat. #. 17502048, Gibco) (500 µℓ) |
| 1 × B27 ™ supplement (Cat. #. 17504-044, Gibco) (1 mℓ) |
| 1 × P/S (Penicillin/Streptomycin) (5 mℓ) |
| 3 µM CHIR 99021 (Cat. #. S1263, Selleckchem, 10 mM stock) (15 µℓ) |
| 10 ng/ FGF10 (Cat. #. 100-26, Peprotech, 100 µg/ mℓ stock) (5 µℓ) |
| 10 ng/ FGF7/KGF (Cat. #. 100-19, Peprotech, 100 µg/ mℓ stock) (5 µℓ) |
| 10 ng/ BMP4 (Cat. #. 120-05, Peprotech, 100 µg/ mℓ stock) (5 µℓ) |
| 50 nM All-trans Retinoic acid (Cat. #. 0695, R&D Systems, 500 µM stock) (5 µℓ) |
| 1/200 Matrigel ® matrix |

<1-8> Day 20 and Thereafter of Differentiation: Three-Dimensional Culture

The cells were collected on day 20, transferred to a low attachment plate, and cultured in the LO medium not containing only Matrigel® matrix among the composition shown in Table 3. Every 2 days during the culture period, half of the medium was replaced with a fresh medium. A three-dimensional lung organoid was finally formed through the three-dimensional culture.

Experimental Example 1: Confirmation of Cell Morphology in 2D Culture and 3D Culture after the 20$^{th}$ Day of Differentiation In the process of differentiation of hPSC cells, the cell morphology was observed by taking pictures when the two-dimensional culture was continued even after the 20$^{th}$ day of the differentiation.

Particularly, cells on days 0, 1, 5, 6, 7, 9 and 13 of the differentiation, cells on days 26, 30 and 33 of the differentiation in which 2D culture was continued, and cells on days 32, 35, 52, 65 and 85 of the differentiation in which the two-dimensional culture was changed to three-dimensional culture after the 20$^{th}$ day of the differentiation were photographed using a microscope, and the cell shape was observed.

Figure 1B:
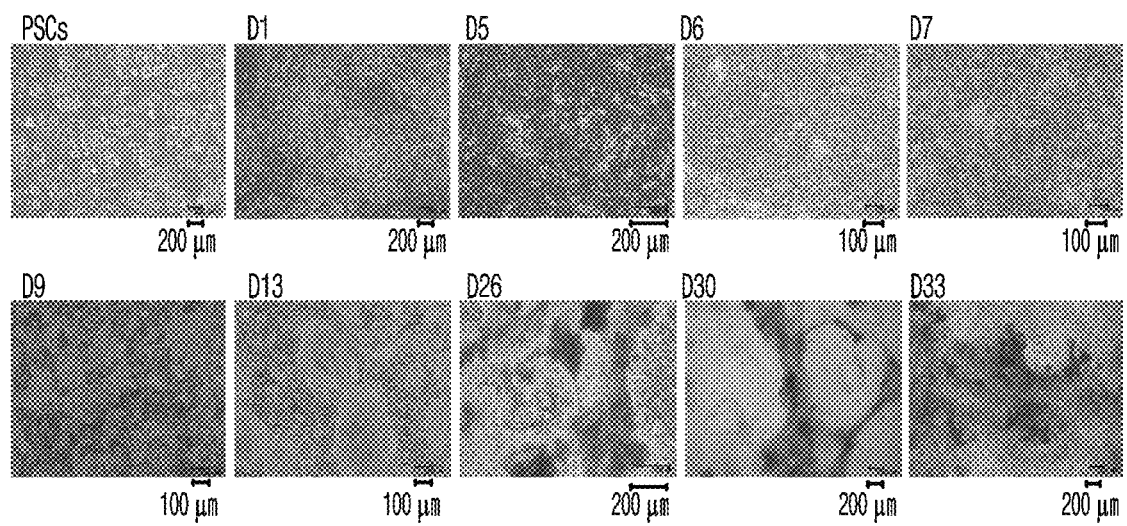
FIG. 1b is a diagram showing the photograph of cell morphology according to the differentiation period of the 2D cultured cells.
Figure 1C:
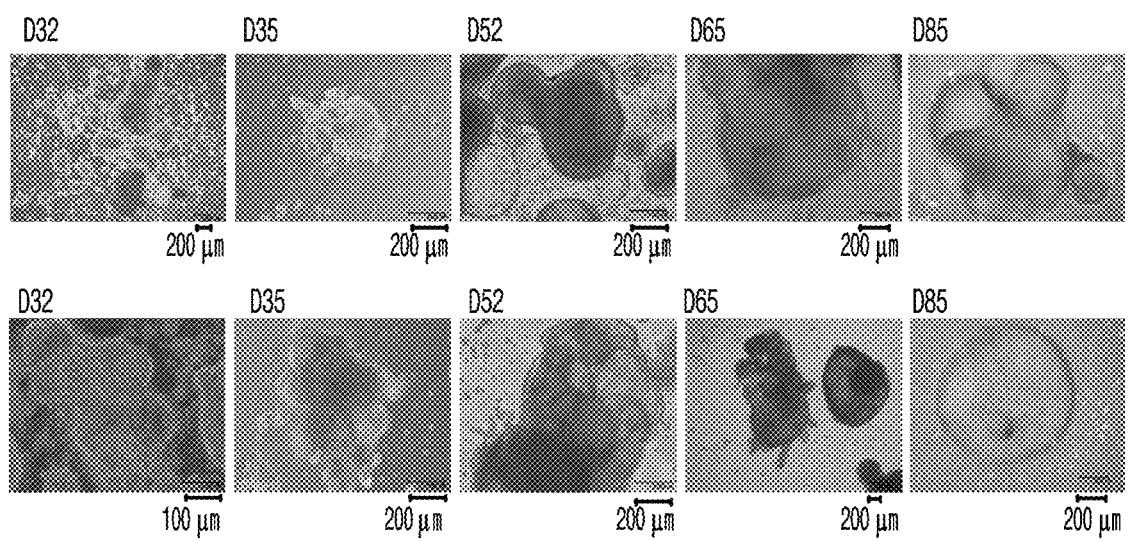
FIG. 1c is a diagram showing the photograph of cell morphology according to the differentiation period of the cells changed to 3D culture on the 20th day of the differentiation.

As a result, when the cells were differentiated by two-dimensional culture until day 33, a cluster-shaped cell aggregate was observed, whereas the cells differentiated by three-dimensional culture after the 20$^{th}$ day of the differentiation without Matrigel® matrix were differentiated into a three-dimensional sphere, similar to that of actual alveolar cells (FIGS. 1b and 1c).

Experimental Example 2: Confirmation of CXCR4 Marker and Mesoendoderm Cell Marker Expression on Day 4 or Day 5 of Differentiation On the 4$^{th}$ or 5$^{th}$ day of differentiation, when the proportion of the cells expressing CXCR4, a complete endoderm (DE) marker, reached 70 to 80%, CXCR4, EpCAM, and CD56 on the cell surface were stained and the degree of differentiation was analyzed by flow cytometry.

Particularly, on the 4$^{th}$ or 5$^{th}$ day of differentiation, the medium of the cells was removed, the cells were washed with DPBS, and then TrypLE™ Express was added thereto, followed by culture for 3 to 5 minutes. Then, TrypLE™ Express was removed, and the cells were collected by adding DPBS, followed by centrifugation at 1,300 rpm for 5 minutes. After removing DPBS, the cells were suspended in FACS buffer. 2 µl of each antibody (CXCR4, cat. #. 551510, BD pharmigen; EpCAM, Cat. #. 324204, Biolegend; CD56, Cat. #. 555518, BD pharmigen) was added to 1×10$^4$~1×10$^5$ cells, followed by reaction at room temperature for 15 to 20 minutes. Then, centrifugation was performed at 3,000 rpm for 3 minutes to remove the supernatant, and 1 ml of fresh FACS buffer was added thereto, and the same procedure was repeated twice. After the last centrifugation, the supernatant was removed, new FACS buffer was added thereto, and the pellet was well suspended. After adding 300 µl of 4% paraformaldehyde, it was stirred well and analyzed by a flow cytometer (Cytoflex, Beckman Coulter). 300 µl of 4% paraformaldehyde was added to each well, and the mixture was stirred well, followed by analysis using a flow cytometer (Cytoflex, Beckman Coulter).

As a result, as shown in FIG. 2a, when the proportion of the cells expressing CXCR4, a complete endoderm (DE) marker, reached 70 to 80%, EpCAM-CD56+ cells were present in a proportion of 15 to 25% of the cells not expressing CXCR4 (CXCR4−) (FIG. 2b). In other references, only CXCR4-expressing cells (CXCR4+) were isolated to prepare organoids, whereas in the present invention, an organoid was prepared by differentiating all CXCR4− and CXCR4+ cells, including mesoendoderm (EpCAM-CD56+) cells, on the 4$^{th}$ and 5$^{th}$ day of differentiation.

Experimental Example 3: Confirmation of Lung Tissue-Specific Gene Expression in the Three-Dimensional Lung Organoid of the Present Invention In order to compare the degree of expression of lung tissue-specific genes in the three-dimensional lung organoid of the present invention according to the differentiation period and the presence or absence of 3D culture, quantitative polymerase chain reaction (qPCR) was performed.

Particularly, RNA was isolated respectively from the cells on days 0, 5 and 20 of the differentiation, the cells on day 30 of the differentiation in which 2D culture was continued after the 20$^{th}$ day of the differentiation, and the lung organoid on day 30 of the differentiation in which the 2D culture was changed to 3D culture after the 20$^{th}$ day of the differentiation in the preparation process of the three-dimensional lung organoid of Example 1. Complementary DNA (cDNA) was synthesized from the RNA using a cDNA synthesis kit (Primescript 1 strand cDNA synthesis kit, Cat. #. 6110A, TAKARA, Japan), and then qPCR (StepOnePlus, Applied Biosystems) was performed using the primers listed in Table 6 and SYBR™ Green Universal Master Mix (Power SYBR™ Green Universal Master Mix, Cat. #. 4367659, Applied Biosystems, USA). The qPCR reaction was performed by repeating the process 40 times at 95° C. for 10 minutes, 95° C. for 15 seconds and 60° C. for 1 minute, and finally, at 95° C. for 15 seconds, 60° C. for 1 minute and 95° C. for 15 seconds.

TABLE 6

| Primer | Sequence (5'→3') | SEQ. ID. NO. |
|---|---|---|
| hNkx2.1 forward | CGGCATGAACATGAGCGGCAT | 1 |
| hNkx2.1 reverse | GCCGACAGGTACTTCTGTTGCTTG | 2 |
| hP63 forward | CCTATAACACAGACCACGCGCAGAA | 3 |
| hP63 reverse | GTGATGGAGAGAGAGCATCGAAG | 4 |
| hSox9 forward | GTACCCGCACTTGCACAAC | 5 |
| hSox9 reverse | TCTCGCTCTCGTTCAGAAGTC | 6 |
| hMucin5AC forward | GCACCAACGACAGGAAGGATGAG | 7 |
| hMucin5AC reverse | CACGTTCCAGAGCCGGACAT | 8 |
| hHOPX forward | GCCTTTCCGAGGAGGAGAC | 9 |
| hHOPX reverse | TCTGTGACGGATCTGCACTC | 10 |
| hSFTPA forward | GTGCGAAGTGAAGGACGTTTGTGT | 11 |
| hSFTPA reverse | TTTGAGACCATCTCTCCCGTCCC | 12 |

As a result, the expressions of the lung tissue-specific genes NKX2.1, P63, Sox9, Mucin 5Ac, HOPX and SFTPA were highest in the lung organoid on the 30$^{th}$ day of the differentiation, in which the 2D culture was changed to 3D culture after the 20$^{th}$ day of the differentiation (FIG. 3). These results indicated that the lung organoid according to the present invention exhibited very similar properties to actual lung tissue.

Experimental Example 4: Confirmation of Lung Tissue-Specific Protein Expression in the Three-Dimensional Lung Organoid of the Present Invention In order to compare the degree of expression of lung tissue-specific proteins in the three-dimensional lung organoid of the present invention according to the differentiation period and the presence or absence of 3D culture, fluorescence-activated cell sorting (FACS) was performed.

Particularly, the cells on days 0 and 20 of the differentiation, and the cells on day 30 of the differentiation in which 2D culture was continued after the 20$^{th}$ day of the differentiation of Example 1 were treated with TrypLE™ Express reagent (Cat. #. 12604013, Gibco) (1 ml/well), reacted at room temperature for 5 minutes, and washed with FACS buffer (5% FBS, 0.1% sodium azide in DPBS). The lung organoid on day 30 of the differentiation in which the 2D culture was changed to 3D culture after the 20$^{th}$ day of the differentiation was treated with 10 mg/ml of collagenase type II (STEMCELL TECHNOLOGIES), reacted three times at 37° C. for 20 minutes, and washed with FACS buffer. Then, FACS analysis was performed using a FACS device (FACSAria II, Becton Dickinson and Company, USA).

As a result, in the cells on day 10 of the differentiation, the expressions of EpCAM, c-Kit, CXCR4, Pro-surfactant protein C and CD90, the markers expressed at the beginning of differentiation, were high, whereas the expressions of these markers were decreased as the differentiation progressed. In the lung organoid on day 30 of the differentiation in which the 2D culture was changed to 3D culture after the 20$^{th}$ day of the differentiation, the lung tissue-specific proteins Sox9 (alveolar epithelial cell marker), PDPN (type 1 alveolar epithelial cell marker), Mucin (goblet cell marker), Surfactant protein C (type 2 alveolar epithelial cell marker) and P63 (basal cell marker) were expressed (FIG. 4).

Experimental Example 5: Confirmation of the Alveolar Structure-Like Morphology of the Three-Dimensional Lung Organoid of the Present Invention The degree of similarity of the three-dimensional lung organoid of the present invention to the actual human lung structure was confirmed by the morphological analysis through the following experiments.

<5-1> Confirmation of Alveolar Structure of Three-Dimensional Lung Organoid

The alveolar structure-like morphology of the three-dimensional lung organoid of the present invention was confirmed by observing the lung organoid under a microscope.

Particularly, the cultured cells on day 20 of the differentiation of Example 1 were mixed with Matrigel® matrix at a volume ratio of 1:1, and seeded in an inner chamber of a trans-well, followed by culture. Then, the cultured lung organoid was observed under a microscope.

As a result, it was confirmed that the lung organoid formed an alveolar shape similar to the actual human lung structure in Matrigel® matrix by branching (FIG. 5a).

<5-2> Confirmation of Alveolar Structure Cross-Section of Three-Dimensional Lung Organoid To confirm the cross section of the branch structure of the three-dimensional lung organoid of Experimental Example <5-1>, DAPI staining was performed.

Particularly, the three-dimensional lung organoid of Experimental Example <5-1> was fixed with 4% paraformaldehyde (PFA), placed on a frozen section mold containing a frozen section embedding agent (FSC22 clear frozen section compound, Cat. #. 3801480, Leica Biosystems, Germany), covered with a frozen section embedding agent, and then frozen at −20° C. The frozen sample was made into 8 μm-thick sections using a freezing microtome, and then placed on a slide and dried. Then, 200 μl of a diluted solution prepared by diluting a drop of DAPI staining reagent (NucBlue™ Fixed Cell Stein Ready Probes™ reagent, Cat. #. R37606, Invitrogen, USA) in 1 ml of PBS was placed on the lung organoid sample, reacted for 5 minutes, and then photographed under a microscope to be observed.

As a result, it was confirmed that the three-dimensional lung organoid consisted of a honeycomb-like structure surrounded by cells forming a thin membrane similar to the human alveolar structure (FIG. 5b).

<5-3> Confirmation of Alveolar Cell-Specific Protein Expression in Three-Dimensional Lung Organoid The expression of the alveolar cell-specific proteins in the three-dimensional lung organoid of Experimental Example <5-1> was confirmed by immunofluorescence.

Particularly, the three-dimensional lung organoid of Experimental Example <5-1> was fixed with 4% PFA, washed with PBS, permeabilized with 0.5% Triton™ X-100 solution (Triton™ X-100 in PBS) for 5 minutes, and then washed three times with 0.1% Triton™ X-100 solution. Anti-surfactant protein B antibody (Cat. #. sc-133143, Santa Cruz Biotechnology, USA) and anti-Sox9 antibody (Cat. #. ab185966, abcam, UK) were diluted in 2% BSA solution dissolved in 0.1% Triton™ X-100 solution, and reacted with the sample at 4° C. for 18~24 hours. Then, the sample was washed three times with 0.1% Triton™ X-100 solution, reacted with the secondary antibody at room temperature for 1 hour, washed, stained with DAPI, and photographed under a microscope to be observed.

Figure 5C:
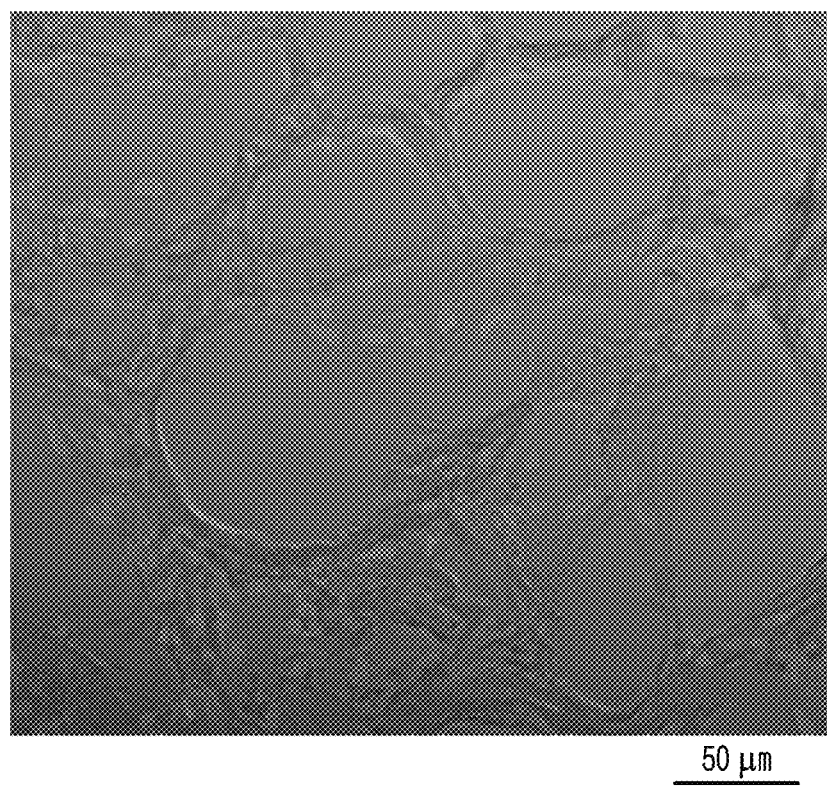
FIG. 5c is a photograph showing the results of immunofluorescence staining confirming the expression of an alveolar cell-specific protein in a three-dimensional lung organoid.

As a result, it was confirmed that surfactant protein B and Sox9, the alveolar cell-specific proteins, were expressed in the three-dimensional lung organoid of the present invention (FIG. 5c).

<5-4> Confirmation of Transmission Electron Microscopy (TEM) Photos of Three-Dimensional Lung Organoid The structure of the three-dimensional lung organoid of Experimental Example <5-1> was observed by taking TEM photos.

Figure 5D:
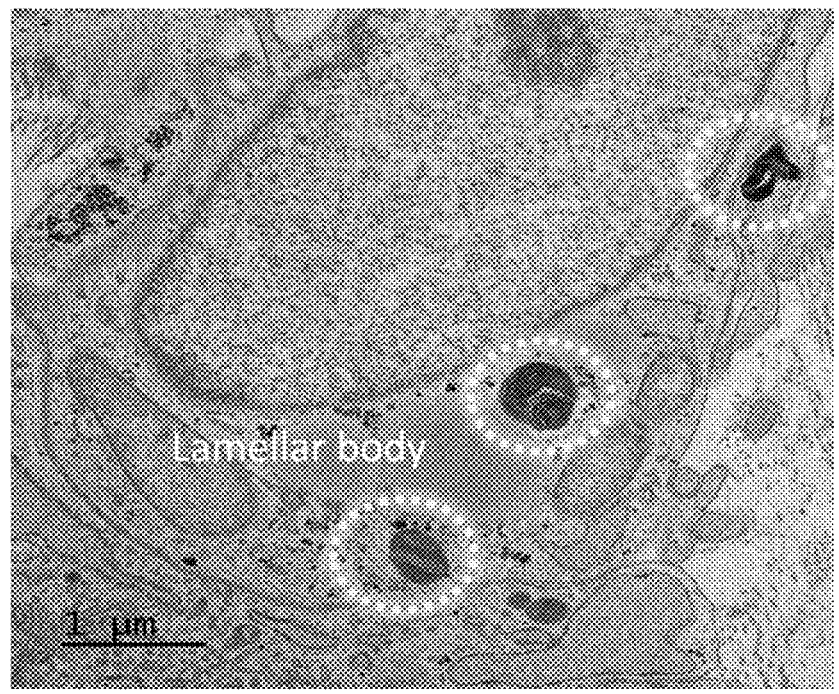
FIG. 5d is a transmission electron microscopy (TEM) image of a three-dimensional lung organoid including an alveolar-specific lamellar body.

As a result, it was confirmed that the alveolar-specific lamellar body were observed in the three-dimensional lung organoid of the present invention (FIG. 5d).

Experimental Example 6: Confirmation of Alveolar Macrophages in the Three-Dimensional Lung Organoid of the Present Invention (1)

Whether alveolar macrophages were differentiated in the three-dimensional lung organoid of the present invention was confirmed by FACS analysis.

Particularly, FACS analysis was performed in the same manner as described in Experimental Example 3, using the antibodies (anti-hHLA-DR-PE, Cat. #. 556644, BD Pharmingen, USA; anti-hCD11b-PerCP-Cy5.5, Cat. #. 301418, Biolegend, USA; anti-hCD11c-PE-Cy7, Cat. #. 561356, BD Pharmingen; anti-hCD68-FITC, Cat. #. 333806, Biolegend; anti-hCD64-APC, Cat. #. 305014, Biolegend; and anti-hCD206-APC/Cy7, Cat. #. 321120, Biolegend) against HLA-DR, CD11b, CD11c, CD68, CD64 and CD206, the human alveolar macrophage markers, in the three-dimensional lung organoids on the $30^{th}$ day, $60^{th}$ day and 1 year of the differentiation.

As a result, it was confirmed that the differentiated alveolar macrophages existed in the three-dimensional lung organoids on the $30^{th}$ day, $60^{th}$ day and 1 year of the differentiation by confirming the expression of the human alveolar macrophage markers in the prepared three-dimensional lung organoid (FIG. 6).

Experimental Example 7: Confirmation of Alveolar Macrophages in the Three-Dimensional Lung Organoid of the Present Invention (2)

Whether the alveolar macrophages were differentiated in the three-dimensional lung organoid of the present invention was confirmed by immunofluorescence staining.

Particularly, immunofluorescence staining was performed with the lung organoid on day 70 of the differentiation in the same manner as described in Experimental Example <5-3>. The lung organoid was double stained with the primary antibodies against pro-surfactant protein C, a type 2 alveolar epithelial cell marker (anti-pro-surfactant protein C rabbit antibody, Cat. #. 400879, abcam) and CD68, an alveolar macrophage marker (anti-hCD68 mouse antibody, Cat. #. ab201340, abcam), washed, reacted with the fluorescent secondary antibodies (Alexa Fluor® 488 anti-rabbit IgG, Cat. #. A11034, Invitrogen; and Alexa Fluor® 647 anti-mouse IgG, Cat. #. A21236, Invitrogen), and observed by taking photographs with a confocal microscope. In addition, the organoid was reacted with the primary antibody against PDPN, a type 1 alveolar epithelial cell marker (anti-PDPN rabbit antibody, Cat. #. sc-59347, Santa Cruz Biotechnology), washed, reacted with Alexa Fluor® 488 anti-rabbit IgG, and observed by taking photographs with a confocal microscope. Further, the organoid was reacted with the primary antibody against CD68, an alveolar macrophage marker (anti-hCD68 mouse antibody, Cat. #. ab201340, abcam), washed, reacted with Alexa Fluor® 488 anti-rabbit IgG, and observed by taking photographs with a confocal microscope.

As a result, the expressions of Pro-surfactant protein C, a type 2 alveolar epithelial cell marker, CD68, an alveolar macrophage marker, and PDPN, a type 1 alveolar epithelial cell marker, were confirmed in the three-dimensional lung organoid of the present invention. Therefore, it was confirmed that alveolar macrophages were also expressed as well as type 1 and type 2 alveolar epithelial cells in the lung organoid of the present invention (FIGS. 7a to 7d).

Experimental Example 8: Confirmation of Morphology and Structure of Three-Dimensional Lung Organoid on 10 Months of Differentiation The morphology of the three-dimensional lung organoid on 10 months of the differentiation was observed by taking photographs with a microscope, and confirmed by performing H&E (hematoxylin and eosin) staining.

Particularly, the three-dimensional lung organoid of Example 1 was cultured until 10 months of the differentiation and observed by taking photographs with a general microscope. In addition, in order to perform H&E staining, the three-dimensional lung organoid was fixed with 4% PFA, washed with PBS, and then sequentially dehydrated using 70%, 90%, 95% and 100% alcohol. Then, the lung organoid was washed with xylene and embedded in paraffin. The paraffin-embedded sections were placed on slides to perform H&E staining, followed by taking photographs with a microscope for observation.

As a result, it was confirmed that there were epithelial cells that form a thin membrane and a lumen surrounded by a thin membrane similar to the human alveolar structure in the three-dimensional lung organoid on 10 months of the differentiation, (FIGS. 8a and 8b).

Experimental Example 9: Confirmation of Gene Expression Pattern According to Three-Dimensional Lung Organoid Morphology The gene expression pattern according to the morphology of the three-dimensional lung organoid according to the present invention was confirmed by RNA sequencing.

Particularly, on the $85^{th}$ day of the differentiation of the three-dimensional lung organoid of Example 1, M type (multi-lineage, round sphere shape), B type (brochioalveolar type, type including branching forms that differentiate) and A type (alveolar type, transparent alveolar-like type) according to three clearly distinguished forms by the naked eye. Transparent alveolar-like) lung organoids were selected, and RNA sequencing of the genes related to respiratory system and macrophages was performed (respiratory system development related genes, GO #. 0060541).

As a result, it was confirmed that the gene expression pattern was different according to the M type, B type and A type, and in particular, it was also confirmed that the expression of the macrophage-related gene (CD68) was strongly expressed in the A type lung organoid (FIGS. 9, 10a, 10b, and 10c).

What is claimed is:

1. A method for fabrication of a lung organoid (LO) comprising alveolar macrophages, which comprises the following steps:
 1) differentiating stem cells to definitive endoderm (DE) cells expressing CXCR4 and mesoendoderm cells expressing EpCAM⁻ CD56⁺, wherein the definitive endoderm cells are contained in a proportion of 70 to 80% of the total cells consisting of both of CXCR4 positive and negative cells, and wherein the mesoendoderm cells do not express CXCR4, and are contained in a proportion of 15 to 25% of the total CXCR4 negative cells;
 2) culturing the definitive endoderm cells and mesoendoderm cells of step 1) in a two-dimensional culture vessel to differentiate into anterior foregut endoderm (AFE) cells;
 3) culturing the AFE cells of step 2) in a two-dimensional culture vessel including a LO formation medium with a solubilized basement membrane matrix; and 4) culturing the cultured cells of step 3) in a three-dimensional culture vessel including a LO formation medium without a solubilized basement membrane matrix, resulting in the formation of alveolar macrophages, wherein the culture of step 4) is performed starting from the 19th to 21st day of the method.

2. The method for fabrication of a lung organoid comprising alveolar macrophages according to claim 1, wherein the stem cells are embryonic stem cells, induced pluripotent stem cells or adult stem cells.

3. The method for fabrication of a lung organoid comprising alveolar macrophages according to claim 1, wherein the culture of step 2) is performed in an anteriorization medium.

4. The method for fabrication of a lung organoid comprising alveolar macrophages according to claim 3, wherein the anteriorization medium contains a TGF-β (transforming growth factor beta) signaling pathway inhibitor and a Wnt signaling pathway inhibitor.

5. The method for fabrication of a lung organoid comprising alveolar macrophages according to claim 4, wherein the TGF-β signaling pathway inhibitor is SB431542 or Noggin.

6. The method for fabrication of a lung organoid comprising alveolar macrophages according to claim 4, wherein the Wnt signaling pathway inhibitor is IWP-2, IWP-3 or IWP-4.

7. The method for fabrication of a lung organoid comprising alveolar macrophages according to claim 1, wherein the LO medium contains a GSK-3β (glycogen synthase kinase 3 beta) inhibitor, a fibroblast growth factor (FGF), a lung branched-type proliferation inhibitor, and an alveolar regeneration activator.

8. The method for fabrication of a lung organoid comprising alveolar macrophages according to claim 7, wherein the GSK-3β inhibitor is CHIR 99021.

9. The method for fabrication of a lung organoid comprising alveolar macrophages according to claim 7, wherein the fibroblast growth factor is FGF10 and FGF7/KGF.

10. The method for fabrication of a lung organoid comprising alveolar macrophages according to claim 7, wherein the lung branched-type proliferation inhibitor is a bone morphogenetic protein (BMP).

11. The method for fabrication of a lung organoid comprising alveolar macrophages according to claim 7, wherein the alveolar regeneration activator is all-trans retinoic acid.

12. The method for fabrication of a lung organoid comprising alveolar macrophages according to claim 1, wherein the three-dimensional culture of step 4) is performed for 10 days to 1 year.

* * * * *

SEQUENCE LISTING

<160> NUMBER OF SEQ ID NOS: 12

<210> SEQ ID NO 1
<211> LENGTH: 21
<212> TYPE: DNA
<213> ORGANISM: Artificial Sequence
<220> FEATURE:
<223> OTHER INFORMATION: hNkx2.1 forward

<400> SEQUENCE: 1
cggcatgaac atgagcggca t                                             21

<210> SEQ ID NO 2
<211> LENGTH: 24
<212> TYPE: DNA
<213> ORGANISM: Artificial Sequence
<220> FEATURE:
<223> OTHER INFORMATION: hNkx2.1 reverse

<400> SEQUENCE: 2
gccgacaggt acttctgttg cttg                                          24

<210> SEQ ID NO 3
<211> LENGTH: 25
<212> TYPE: DNA
<213> ORGANISM: Artificial Sequence
<220> FEATURE:
<223> OTHER INFORMATION: hP63 forward

<400> SEQUENCE: 3
cctataacac agaccacgcg cagaa                                         25

<210> SEQ ID NO 4
<211> LENGTH: 23
<212> TYPE: DNA
<213> ORGANISM: Artificial Sequence
<220> FEATURE:
<223> OTHER INFORMATION: hP63 reverse

<400> SEQUENCE: 4
gtgatggaga gagagcatcg aag                                           23

<210> SEQ ID NO 5
<211> LENGTH: 19
<212> TYPE: DNA
<213> ORGANISM: Artificial Sequence
<220> FEATURE:
<223> OTHER INFORMATION: hSox9 forward

<400> SEQUENCE: 5
gtacccgcac ttgcacaac                                                19

<210> SEQ ID NO 6
<211> LENGTH: 21
<212> TYPE: DNA
<213> ORGANISM: Artificial Sequence
<220> FEATURE:
<223> OTHER INFORMATION: hSox9 reverse

<400> SEQUENCE: 6
tctcgctctc gttcagaagt c                                             21

<210> SEQ ID NO 7
<211> LENGTH: 23
<212> TYPE: DNA
<213> ORGANISM: Artificial Sequence

```
<220> FEATURE:
<223> OTHER INFORMATION: hMucin5AC forward

<400> SEQUENCE: 7
gcaccaacga caggaaggat gag                                           23

<210> SEQ ID NO 8
<211> LENGTH: 20
<212> TYPE: DNA
<213> ORGANISM: Artificial Sequence
<220> FEATURE:
<223> OTHER INFORMATION: hMucin5AC reverse

<400> SEQUENCE: 8
cacgttccag agccggacat                                               20

<210> SEQ ID NO 9
<211> LENGTH: 19
<212> TYPE: DNA
<213> ORGANISM: Artificial Sequence
<220> FEATURE:
<223> OTHER INFORMATION: hHOPX forward

<400> SEQUENCE: 9
gcctttccga ggaggagac                                                19

<210> SEQ ID NO 10
<211> LENGTH: 20
<212> TYPE: DNA
<213> ORGANISM: Artificial Sequence
<220> FEATURE:
<223> OTHER INFORMATION: hHOPX reverse

<400> SEQUENCE: 10
tctgtgacgg atctgcactc                                               20

<210> SEQ ID NO 11
<211> LENGTH: 24
<212> TYPE: DNA
<213> ORGANISM: Artificial Sequence
<220> FEATURE:
<223> OTHER INFORMATION: hSFTPA forward

<400> SEQUENCE: 11
gtgcgaagtg aaggacgttt gtgt                                          24

<210> SEQ ID NO 12
<211> LENGTH: 23
<212> TYPE: DNA
<213> ORGANISM: Artificial Sequence
<220> FEATURE:
<223> OTHER INFORMATION: hSFTPA reverse

<400> SEQUENCE: 12
tttgagacca tctctcccgt ccc                                           23
```